United States Patent
Sorge et al.

(10) Patent No.: US 6,803,201 B2
(45) Date of Patent: Oct. 12, 2004

(54) COMPOSITIONS AND METHODS FOR POLYNUCLEOTIDE SEQUENCE DETERMINATION

(75) Inventors: Joseph A. Sorge, Wilson, NY (US); Bahram Arezi, Encinitas, CA (US); Holly Hogrefe, San Diego, CA (US)

(73) Assignee: Stratagene, La Jolla, CA (US)

( * ) Notice: Subject to any disclaimer, the term of this patent is extended or adjusted under 35 U.S.C. 154(b) by 0 days.

(21) Appl. No.: 10/056,598

(22) Filed: Jan. 24, 2002

(65) Prior Publication Data

US 2003/0149257 A1 Aug. 7, 2003

(51) Int. Cl.[7] .......................... C12Q 1/68; C12P 19/34; C07H 21/04; C07H 19/04
(52) U.S. Cl. ..................... 435/6; 435/91.1; 435/91.2; 536/23.1; 536/24.3; 536/24.32; 536/25.32; 536/26.6
(58) Field of Search .................. 435/6, 91.1, 91.2, 435/810, 24.33; 536/23.1, 24.3, 24.33, 24.32, 25.32, 26.6, 243

(56) References Cited

U.S. PATENT DOCUMENTS

| 5,888,819 A | * | 3/1999 | Goelet et al. ................. 435/5 |
| 5,945,283 A | * | 8/1999 | Kwok et al. ................... 435/6 |
| 6,013,431 A | * | 1/2000 | Soderlund et al. ............. 435/5 |
| 6,177,249 B1 |  | 1/2001 | Kwok et al. ................... 435/6 |
| 6,287,778 B1 | * | 9/2001 | Huang et al. .................. 435/6 |
| 6,316,200 B1 | * | 11/2001 | Nadeau et al. ................ 435/6 |

FOREIGN PATENT DOCUMENTS

| EP | 0 648 280 B1 |   | 5/1999 | ............ C12Q/1/68 |
| WO | WO 01/32887 | * | 5/2001 |  |
| WO | WO 01/32887 A1 |   | 5/2001 | ........... C12N/15/54 |

OTHER PUBLICATIONS

International Search Report of International Application No. PCT/US03/02117.

* cited by examiner

Primary Examiner—Kenneth R. Horlick
Assistant Examiner—Cynthia B. Wilder
(74) Attorney, Agent, or Firm—Palmer & Dodge LLP; Kathleen M. Williams

(57) ABSTRACT

The present invention relates to a method for identifying a nucleotide at a predetermined location on a target polynucleotide. The method involves single nucleotide extension reaction comprising an oligonucleotide primer comprising a first sequence and a second sequence or a tag. The method may further comprises a probe which hybridizes to the second sequence or an anti-tag molecule which interacts with the tag, where the hybridization or interaction causes a detectable signal transfer which is indicative of the identity of the nucleotide base at the predetermined location. The invention further provides compositions and kits for performing the subject method of the invention.

41 Claims, 6 Drawing Sheets

COMPOSITIONS AND METHODS FOR POLYNUCLEOTIDE SEQUENCE DETERMINATION

FIELD OF THE INVENTION

This invention relates to the field of polynucleotide sequence determination, in particular, relates to determine the identity of a single nucleotide in a target polynucleotide sequence, e.g., single nucleotide polymorphism ("SNP") analysis.

BACKGROUND

Techniques for the analysis of polynucleotide sequences have found widespread use in basic research, diagnostics, and forensics. Single nucleotide detection is applied in processes including the detection of single nucleotide polymorphisms, identification of single base changes, speciation, determination of viral load, genotyping, medical marker diagnostics, and the like.

Single nucleotide detection can be accomplished by a number of methods. Most methods rely on the use of the polymerase chain reaction (PCR) to amplify the amount of target DNA. One of the first developed PCR-dependent methods is restriction site polymorphism detection, where the PCR product is cleaved by a restriction enzyme and then analyzed by electrophoresis. Another early method is allele-specific PCR in which one of the PCR primers is designed such that it will discriminate at its 3' end between DNA targets having a sequence that perfectly matches the primer from those targets not perfectly matching the primer.

TaqMan was the first homogenous assay capable of detecting single nucleotide polymorphisms (U.S. Pat. No. 5,723,591). In this assay, two PCR primers flank a central probe oligonucleotide. The probe oligonucleotide comprises two fluorescent moieties. During the polymerization step of the PCR process, the polymerase cleaves the probe oligonucleotide. The cleavage causes the two fluorescent moieties to become physically separated, which causes a change in the wavelength of the fluorescent emission. As more PCR product is created, the intensity of the novel wavelength increases. While TaqMan accomplishes the goal of single nucleotide detection in a homogenous assay, it has two disadvantages. The first is that each nucleotide to be detected requires a different oligonucleotide probe comprising two different fluorescent moieties. Such probes must be custom-synthesized and are thus expensive. The second disadvantage is that TaqMan probes are not very discriminating for single nucleotide differences. Thus there can be significant false-positive signals.

Molecular Beacons are an alternative to TAQMAN (U.S. Pat. Nos. 6,277,607; 6,150,097; 6,037,130). Molecular Beacons undergo a conformational change upon binding to a perfectly matched template. The conformational change of the Beacon increases the physical distance between a fluorophore moiety and a quencher moiety on the Beacon. This increase in physical distance causes the effect of the quencher to be diminished, thus increasing the signal derived from the fluorophore. Molecular Beacons are more discriminating of single nucleotide differences, as compared with TaqMan probes. However they still require the synthesis of a custom oligonucleotide (the Beacon) having two different fluorescent moieties for each target sequence being examined. Thus the technology is expensive.

There are several other fluorescent and enzymatic PCR technologies, such as SCORPIONS™, SUNRISE™ primers, and DNAzymes. Not all of these are suitable for single nucleotide detection, and most of them require the synthesis of a custom, fluorescently labeled oligonucleotide for each target nucleotide.

Hybridization to a "DNA chip" is another way of detecting single nucleotide differences (U.S. Pat. No. 5,856,104). Typically oligonucleotides that are complementary to the suspected target DNAs are synthesized on a solid surface ("chip" or "oligonucleotide array"). The target DNA is PCR amplified, labeled, and then hybridized to the oligonucleotide array. Ideally, perfectly matched PCR fragments will hybridize to the array, but mismatched fragments will not. While the technology, in theory, offers the opportunity to look at many different loci simultaneously, in practice the need to amplify the target DNA using PCR limits the degree to which the assay can be multiplexed. In addition the start-up costs for designing an oligonucleotide microarray can be very expensive. Lastly, the frequency of false-positive and false-negative spots is very high, and necessitates the use of many surface-bound oligonucleotides for each target DNA sequence.

There currently are two non-PCR based technologies capable of detecting single nucleotide changes in complex genomes. The Invader-Squared method (U.S. Pat. No. 6,001,567) utilizes a cascade of DNA cleavage reactions. While sensitive, it requires the synthesis of several long, target-specific oligonucleotides in addition to several detection oligonucleotides. The rolling circle detection method (Lizardi et al., Nature Genetics 19: 225–232) utilizes a target nucleotide-specific ligation reaction to create a circular template that is then replicated with a polymerase in rolling-circle fashion. One of the advantages is that the reaction does not require thermal cycling. One drawback is that ligation reactions are not highly specific for single nucleotide detection.

Single base extension ("SBE"; also called minisequencing) is a technology that uses dideoxy chain terminators in combination with a DNA polymerase to determine the identity of a single nucleotide in a target DNA sample that has been PCR amplified (Syvanen et al., 1990, Genetics 8:684–642; U.S. Pat. No. 5,888,819; Euoropean patent application EP 0648280 A1, each of which is incorporated herein by reference). The technology uses a DNA primer that is hybridized to a target polynucleotide in the presence of dideoxy chain terminators, but typically in the absence of deoxynucleotide triphosphates. A DNA polymerase will add a single dideoxy chain terminator to the 3' end of a primer that is reasonably hybridized to the DNA target. The polymerase incorporates the appropriate dideoxy terminator determined by the complementary sequence in the target polynucleotide. Thus, the identity of the dideoxy terminator that is incorporated reflects the identity of the nucleotide within the target polynucleotide that is immediately adjacent to the target nucleotide that is hybridized with the 3' nucleotide of the primer.

There are a number of patents and patent applications for SBE. In U.S. Pat. No. 6,013,431, the dideoxy chain terminators would be labeled with reporter moieties, such as fluorescent molecules, and the incorporation of a label into a primer is measured by gel electrophoresis. The method described in U.S. Pat. Nos. 6,015,675; 5,582,989; 5,578,458 relates to placing the primer on a solid surface, such as a chip. The chip is exposed to a solution containing the target polynucleotide plus fluorescently labeled dideoxy chain terminators and polymerase. When a single labeled base is added to the bound primer, the probe begins to fluoresce.

Fluorescence polarization has been used to perform SBE. With this approach the chain terminators are fluorescently labeled as with other methods. However rather than separating the labeled primers by gel electrophoresis or physical separation, the incorporated chain terminators are generated by shining polarized light on the sample, and then detecting the polarization of the emitted fluorescent light. Fluorescent light emitted by unincorporated terminators will not be polarized because these small molecules are rapidly moving in solution. However labeled terminators that have been incorporated onto the end of a primer will be moving more slowly and tend to emit polarized light. Thus the degree to which the emitted light is polarized reflects the degree to which there has been incorporation of a dideoxy chain terminator onto the end of a primer. The color of the polarized emitted light reflects the particular dideoxy terminator (A, C, G, or T) that was incorporated onto the 3' end of the primer. The advantage to the fluorescent polarization method is that it is homogeneous (all done in a single test tube). However the input target DNA is typically a PCR fragment, and the PCR reaction needs to be performed prior to SBE. Moreover the PCR product needs to be separated from the PCR primers and deoxynucleotides of the PCR reaction prior to performing the SBE reaction.

Another homogenous method has been described in U.S. Pat. No. 6,177,249. This patent uses fluorescence resonance energy transfer ("FRET") (Wittwer, et al., 1997, Biotechniques 22:130–138; Bernard, et al., 1998, Am. J. Pathol. 153:1055–1061). FRET occurs when two fluorescent molecules are in close physical proximity (e.g., 10–100 Å), and one of the fluorescent molecules can absorb light of a wavelength that is emitted by the other fluorescent molecule. For example, suppose the first fluorescent molecular is stimulated by blue light and emits green light, and the second fluorescent molecule is stimulated by green light and emits red light. If, for example, an oligonucleotide contains both fluorescent molecules and the primer is illuminated with blue light, it will emit red light without emitting much green light. In U.S. Pat. No. 6,177,249 (supra), the SBE primer contains one fluorescent molecule. The dideoxy chain terminators contain another (up to 4 different) fluorescent molecules. Upon addition of a terminator to the 3' end of a primer, FRET can occur. As per the FRET example above, stimulating blue light would be converted to green light by the fluorophore on the primer, and then would be further converted to red light after a terminator has been added to the primer. The emission of red light would be used to monitor the degree to which terminators have been added to the primer. One would use 4 terminators with 4 different emission spectra, but all capable of being stimulated by the wavelength released by the primer-bound fluorophore. The advantage to this method is that it is a homogenous assay, although still requiring a PCR amplification pre-SBE step for complex genomes. The disadvantage is that the user must synthesize an expensive, custom oligonucleotide primer for each target DNA locus being examined.

SUMMARY OF THE INVENTION

The present invention relates to compositions and methods for the detection of nucleotides at predetermined locations on a polynucleotide of interest. The embodiments of the invention include compositions and methods in which a primer extension reaction is designed to extend a single nucleotide (single base extension, SBE) and the incorporation of a labeled chain terminator is determined by signal transfer.

The invention provides a composition for identifying a nucleotide at a predetermined position of a target polynucleotide in a sample, the composition comprising:

(a) an oligonucleotide primer comprising a first sequence which hybridizes to the target polynucleotide immediately 3' of the nucleotide, and a second sequence which does not hybridize to the target polynucleotide in the presence of a third sequence; and (b) an oligonucleotide probe comprising the third sequence which hybridizes to the second sequence of the oligonucleotide primer, the oligonucleotide probe labeled with a first member of a pair of interactive labels.

The second sequence of the oligonucleotide primer is preferably located at the 5' terminal of the first sequence.

The composition of the invention may also comprise a first polynucleotide chain terminator, which is incorporated in a template-dependent manner into the oligonucleotide primer by a polynucleotide synthesis enzyme.

The composition of the invention may further comprise one or more of a second, a third and/or a fourth polynucleotide chain terminator, where the first, second, third and fourth polynucleotide terminators are not identical.

The composition of the invention may still further comprises a template-dependent polynucleotide synthesis enzyme for incorporating in a template-dependent manner a complementary polynucleotide chain terminator into the oligonucleotide primer.

Preferably, the first polynucleotide chain terminator of the subject composition is labeled with a second member of the pair of interactive labels.

In a preferred embodiment, one member of the pair of interactive labels is a quencher molecule.

In one embodiment of the invention, the first and second members of the pair of interactive labels interact with each other to generate a signal by fluorescent resonance energy transfer.

Preferably, the first and second members of the pair of interactive labels are fluorescent molecules which interact with each other to generate a signal by fluorescent resonance energy transfer.

Also preferably, the polynucleotide synthesis enzyme of the subject composition is a JDF-3 DNA polymerase.

In one embodiment of the invention, the oligonucleotide primer comprises a separation moiety that permits separation of the oligonucleotide primer and/or the oligonucleotide probe hybridized to the primer from unincorporated polynucleotide chain terminator, and oligonucleotide probe which is not hybridized to the oligonucleotide primer.

Preferably, the composition of the subject invention also provides a target moiety specific for the separation moiety, where the separation moiety binds to the target moiety to permit the separation.

The target moiety of the composition is preferably attached to a solid support.

The invention provides another composition for identifying a nucleotide at a predetermined position of a target polynucleotide in a sample, the composition comprising:

(a) an oligonucleotide primer comprising a first sequence which hybridizes to the target polynucleotide immediately 3' of the nucleotide, and is covalently attached to a tag molecule; and (b) an anti-tag molecule which binds to the tag molecule, the anti-tag molecule labeled with a first member of a pair of interactive labels.

The tag molecule of the subject composition is preferably located on the 5' terminal of the oligonucleotide primer.

Preferably, the tag molecule is a first member of a specific binding pair which comprises the first member and a second member.

Also preferably, the anti-tag molecule is the second member of the specific binding pair.

In one embodiment, the specific binding pair is a biotin-streptavidin pair.

The invention provides a kit for identifying a nucleotide at a predetermined position of a target polynucleotide in a sample, the kit comprising:
  (a) an oligonucleotide primer comprising a first sequence which hybridizes to the target polynucleotide immediately 3' of the nucleotide, and a second sequence which does not hybridize to the target polynucleotide in the presence of a third sequence;
  (b) an oligonucleotide probe comprising the third sequence which hybridizes to the second sequence of the oligonucleotide primer, the oligonucleotide probe labeled with a first member of a pair of interactive labels; and
  (c) packaging materials therefore.

The kit of the subject invention may also comprise a polynucleotide chain terminator, which can be incorporated in a template-dependent manner into the oligonucleotide primer by a polynucleotide synthesis enzyme.

The kit of the subject invention may further comprise one or more of a second, a third and/or a fourth polynucleotide chain terminator, where the first, second, third and fourth polynucleotide terminators are not identical.

The polynucleotide chain terminator of the kit is preferably labeled with a second member of the pair of interactive labels.

The kit of the subject kit may still further comprise a template-dependent polynucleotide synthesis enzyme for incorporating in a template-dependent manner a complementary polynucleotide chain terminator into the oligonucleotide primer.

Preferably, the polynucleotide synthesis enzyme is a JDF-3 DNA polymerase.

The invention provides a kit for identifying a nucleotide at a predetermined position of a target polynucleotide in a sample, the kit comprising:
  (a) an oligonucleotide primer comprising a first sequence which hybridizes to the target polynucleotide immediately 3' of the nucleotide, and is covalently attached to a tag molecule;
  (b) an anti-tag molecule which binds to the tag molecule, the anti-tag molecule being labeled with a first member of a pair of interactive labels; and
  (c) packaging materials therefore.

The tag molecule of the subject kit is preferably a first member of a specific binding pair which comprises the first member and a second member.

Preferably, the anti-tag molecule is the second member of the specific binding pair.

In one embodiment of the invention, the specific binding pair comprises a biotin-streptavidin pair.

The invention provides a method of identifying the presence of a nucleotide at a predetermined position of a target polynucleotide, the method comprising:
  (a) incubating the target polynucleotide in a reaction mixture comprising an oligonucleotide primer which hybridizes to the target polynucleotide immediately 3' of the nucleotide, an oligonucleotide probe which hybridizes to the oligonucleotide primer and labeled with a first member of a pair of interactive labels, a polynucleotide chain terminator labeled with a second member of the pair of interactive labels, where the incubating permits the polynucleotide chain terminator to be incorporated into the oligonucleotide primer, and permits the oligonucleotide probe to hybridize to the oligonucleotide primer to permit the pair of interactive labels to generate a signal; and
  (b) detecting the signal, where the detection is indicative of the presence of the nucleotide in the target polynucleotide.

The invention also provides a method of identifying the presence of a nucleotide at a predetermined position of a target polynucleotide, the method comprising the steps:
  (a) incubating the target polynucleotide in a reaction mixture comprising an oligonucleotide primer which hybridizes to the target polynucleotide immediately 3' of the nucleotide and a polynucleotide chain terminator labeled with a second member of a pair of interactive labels, where the incubating permits the polynucleotide chain terminator to be incorporated into the oligonucleotide primer;
  (b) incubating the oligonucleotide primer comprising the second member of the pair of interactive labels with an oligonucleotide probe labeled with a first member of the pair of interactive labels, such that formation of a hybrid between the oligonucleotide probe and the primer permits the pair of interactive labels to a generate a signal; and
  (c) detecting the signal, where the detection is indicative of the presence of the nucleotide in the target polynucleotide.

In one embodiment of the invention, the signal is generated by fluorescent resonance energy transfer.

In a preferred embodiment, the oligonucleotide primer comprises a first sequence which hybridizes to the target polynucleotide and a second sequence which does not hybridize to the target polynucleotide in the presence of a third sequence.

Preferably, the second sequence on the oligonucleotide primer is located at the 5' terminal of the first sequence.

Also preferably, the oligonucleotide probe comprises the third sequence which hybridizes to the second sequence of the oligonucleotide primer.

In one embodiment, the polynucleotide chain terminator is incorporated by a polynucleotide synthesis enzyme.

The reaction mixture of the subject method may also comprise one or more of a second, a third and/or a fourth polynucleotide chain terminator, where the first, second, third and fourth polynucleotide terminators are not identical.

Preferably, the polynucleotide synthesis enzyme is a JDF-3 DNA polymerase.

The oligonucleotide primer of the subject method may comprise a separation moiety that permits separation of the oligonucleotide primer from the reaction mixture.

Preferably, a target moiety is provided in the subject method for the separation moiety to form a specific binding pair for separation.

In one embodiment, the target moiety is attached to a solid support.

The invention provides a method for identifying the presence of a nucleotide at a predetermined position of a target polynucleotide, the method comprising:
  (a) incubating the target polynucleotide in a reaction mixture comprising an anti-tag molecule labeled with a first member of a pair of interactive labels, a polynucleotide chain terminator labeled with a second member of the pair of interactive labels, and an oligonucleotide primer which hybridizes to the target polynucleotide immediately 3' of the nucleotide, the oligonucleotide primer covalently coupled to a tag molecule, where the incubating permits the polynucleotide chain terminator to be incorporated into the oligonucleotide primer, and the incubating also permits the anti-tag molecule to interact with the tag molecule on the oligonucleotide primer, so that the pair of interactive labels generate a signal; and (b) detecting the signal, where the detection is indicative of the presence of the nucleotide in the target polynucleotide.

In a preferred embodiment, the signal is generated by fluorescent resonance energy transfer.

In another preferred embodiment, one member of the pair of interactive labels is a quencher molecule.

Preferably, the tag molecule is located at 5' terminal of the oligonucleotide primer.

The tag molecule of the subject method may comprise a first member of a specific binding pair which comprises the first member and a second member.

The anti-tag molecule may comprise the second member of the specific binding pair.

In one embodiment, the specific binding pair is a biotin-streptavidin binding pair.

The chain terminator of the invention may be one selected from the group consisting of: a dideoxynucleotide triphosphate, a ribofuranose analog, a reversible nucleotide terminator, and an acyclic terminator.

The target polynucleotide of the invention may present in a sample.

DETAILED DESCRIPTION OF THE INVENTION

Definitions

Figure 1:
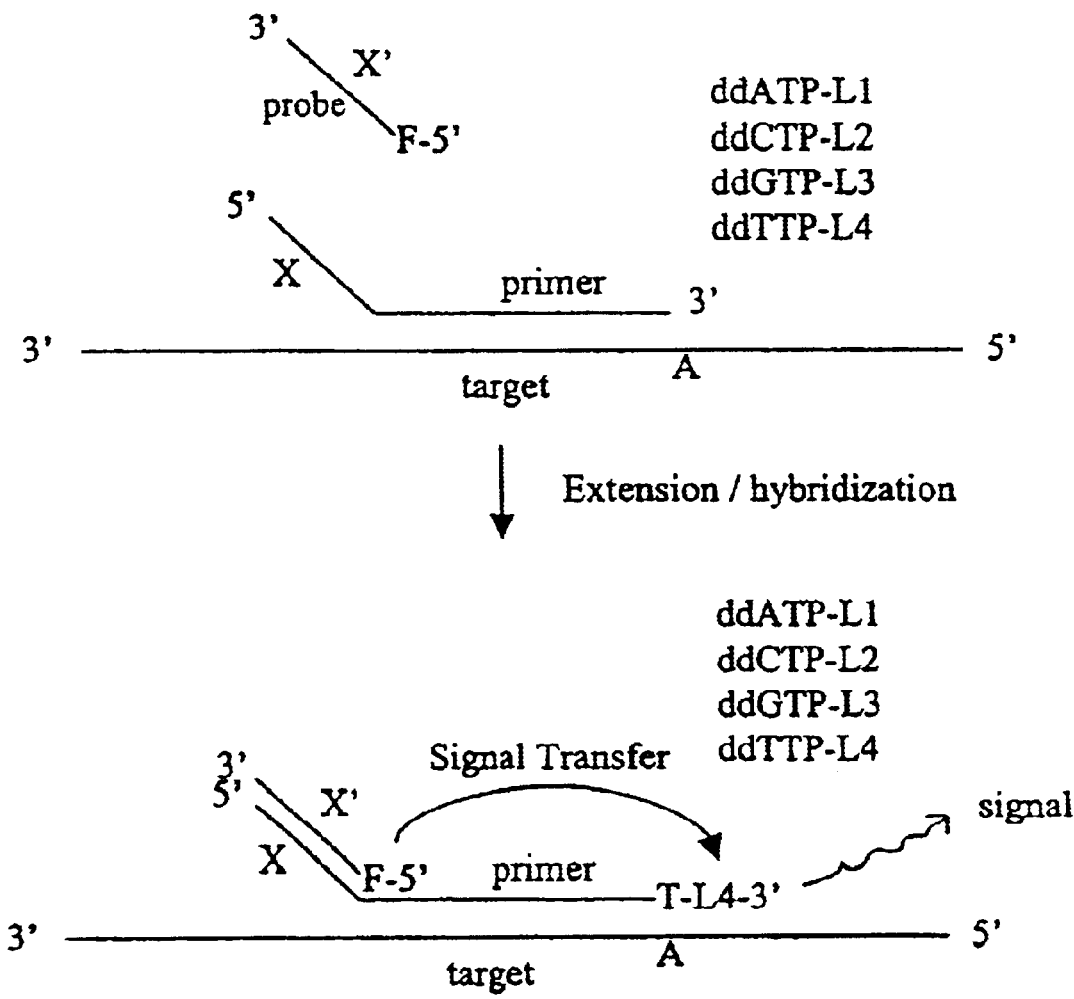
FIG. 1 illustrates the hybridization of an oligonucleotide probe comprising a third sequence which hybridizes to an oligonucleotide primer comprising a first and a second sequences and an incorporated chain terminator in one embodiment of the invention. The probe is labeled with a first member of a pair of interactive labels. Chain terminators (L1 to L4) are used, each labeled with a different second member of the pair of interactive labels. Each terminator will emit a different signal (e.g., color) when stimulated by the stimulus (F) coming from the oligonucleotide probe. The signal form each terminator is generated by FRET.
Figure 2:
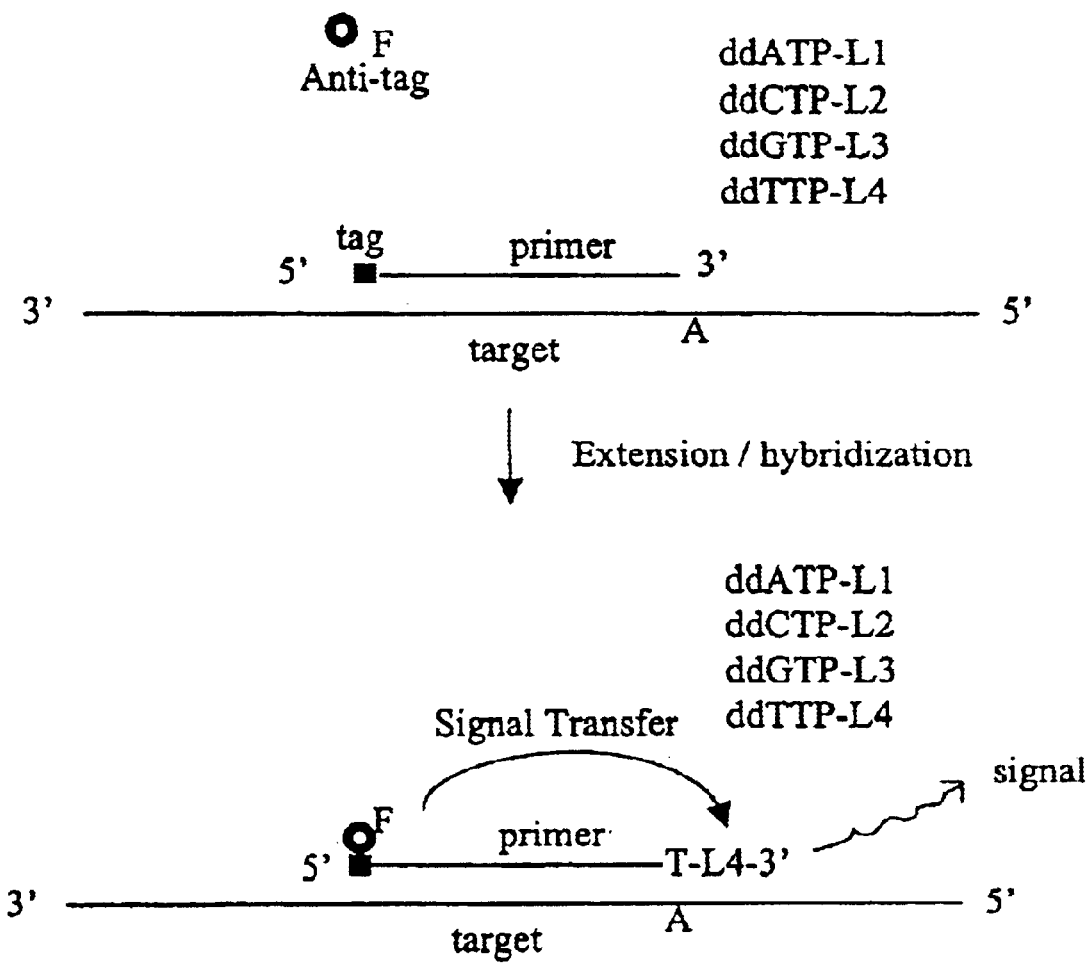
FIG. 2 illustrates the use of a tag and anti-tag pair to replace the primer-probe interaction of FIG. 1 in one embodiment of the invention.
Figure 3:
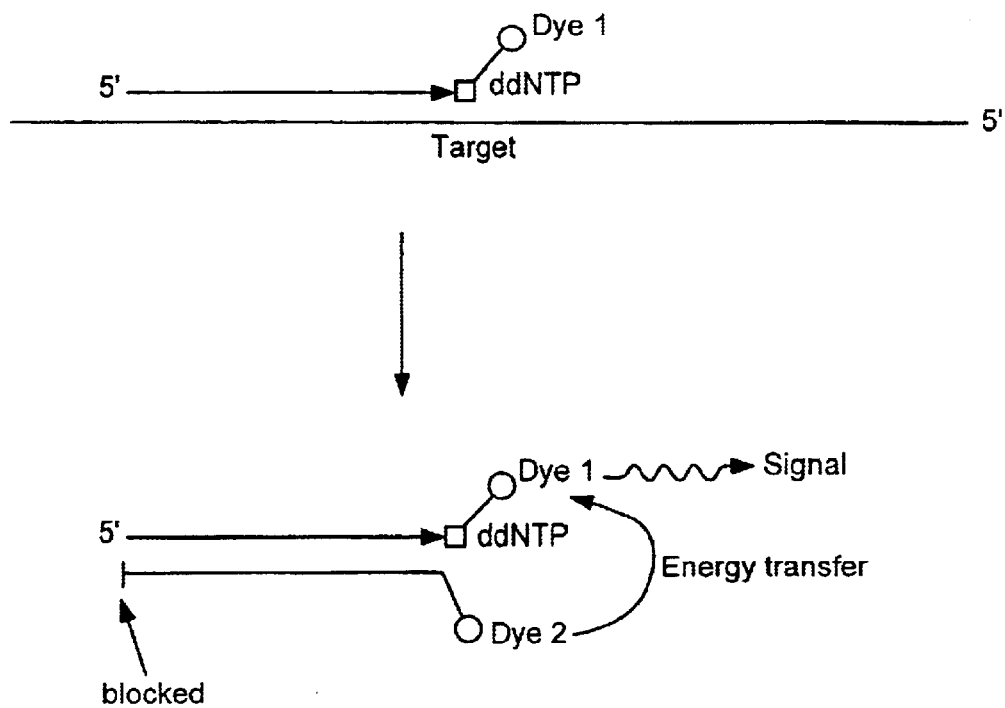
FIG. 3 illustrates the use of an oligonucleotide probe which is fully complementary to the oligonucleotide primer in one embodiment. FRET signal is generated between two members (dye 1 and dye 2) of a pair of interactive labels present on ddNTP and the probe.

"Target polynucleotide" refers to a polynucleotide having a sequence, to which the presence or absence or identity of at least one nucleotide is to be determined, i.e., by primer extension, conventional sequencing or mini-sequencing. In the context of a preferred application of the method according to the present invention, a target polynucleotide comprises a nucleotide at a predetermined position of the target polynucleotide whose presence or absence or identity in the target polynucleotide is to be determined. The terms "nucleotide" and "nucleotide base" are used interchangeably. A target polynucleotide may be a length between 10 kb and 10 base pairs, e.g., 1 kb-50 base pairs, or 500 base pairs-100 base pairs. A target polynucleotide of the invention may be a naturally occurring polynucleotide (i.e., one existing in nature without human intervention), or a recombinant polynucleotide (i.e., one existing only with human intervention).

According to the invention, a nucleotide can be modified, biotinylated, radiolabeled, and the like and also include phosphorothioate, phosphite, ring atom modified derivatives, and the like. The term "nucleotide" includes the derivatives and analogs thereof and includes dNTPs and ddNTPs.

A nucleotide "position" as used herein refers to the location of a given single base within a polynucleotide, including an oligonucleotide.

A "polynucleotide" is a covalently linked sequence of nucleotides (i.e., ribonucleotides for RNA and deoxyribonucleotides for DNA) in which the 3' position of the pentose of one nucleotide is joined by a phosphodiester group to the 5' position of the pentose of the next. "Polynucleotide" includes, without limitation, single- and double-stranded polynucleotide. The term "polynucleotide" as it is employed herein embraces chemically, enzymatically or metabolically modified forms of polynucleotide. "Polynucleotide" also embraces a short polynucleotide, often referred to as an oligonucleotide.

A polynucleotide or an oligonucleotide (e.g., the oligonucleotide primer or the oligonucleotide probe) has a "5'-terminus" (5' end) and a "3'-terminus" (3' end) because polynucleotide phosphodiester linkages occur to the 5' carbon and 3' carbon of the pentose ring of the substituent mononucleotides. The end of a polynucleotide at which a new linkage would be to a 5' carbon is its 5' terminal nucleotide. The end of a polynucleotide at which a new linkage would be to a 3' carbon is its 3' terminal nucleotide. A terminal nucleotide, as used herein, is the nucleotide at the end position of the 3'- or 5'-terminus. As used herein, a polynucleotide sequence, even if internal to a larger polynucleotide (e.g., a sequence region within a polynucleotide), also can be said to have 5'- and 3'-ends.

Oligonucleotides are typically less than 150 nucleotides long (e.g., between 5 and 150, preferably between 10 to 100, more preferably between 15 to 50 nucleotides in length), however, as used herein, the term is also intended to encompass longer or shorter polynucleotide chains. Oligonucleotides can form secondary and tertiary structures by self-hybridizing or by hybridizing to other polynucleotides, therefore serving as primers for polynucleotide chain extension. Such structures can include, but are not limited to, duplexes, hairpins, cruciforms, bends, and triplexes.

As used herein, an "oligonucleotide primer" is an oligonucleotide comprising a sequence complementary to a target polynucleotide. An oligonucleotide, according to the invention, hybridizes to a target polynucleotide through base pairing so to initiate an elongation (extension) reaction to incorporate a nucleotide into the oligonucleotide primer. An "oligonucleotide primer" according to the present invention, may comprise a first sequence that hybridizes to a target polynucleotide immediately 3' of a nucleotide at a predetermined location. An "oligonucleotide primer" may comprise a first sequence which hybridizes to a target polynucleotide and a second sequence which does not hybridize to the target polynucleotide in the presence of a third sequence. The first sequence or the second sequence of an oligonucleotide may be between 10 to 100 nucleotides in length, preferably between 15–50 nucleotides in length. A common second sequence may be used for a number of oligonucleotide primers comprising the same first sequence. An oligonucleotide primer useful in the present invention may be covalently coupled to a tag molecule.

An "oligonucleotide probe" is an oligonucleotide comprising a third sequence which is complementary to the oligonucleotide primer. One or more oligonucleotide probes can be made, each comprising a different sequence complementary to the oligonucleotide primer. An "oligonucleotide probe" according to the invention, may be between 10 to 100 nucleotides in length, preferably between 15–50 nucleotides in length. When an oligonucleotide probe is designed to complement to a common second sequence on a number of oligonucleotide primers, the oligonucleotide probe is also referred to as a universal probe for the number of oligonucleotide primers.

As used herein, an "oligonucleotide hybridizing to a target polynucleotide immediately 3' of a nucleotide" is an oligonucleotide comprising a first sequence that is complementary to the target polynucleotide. The oligonucleotide has a 3' terminal nucleotide complementary to the nucleotide next to the 3' end of the nucleotide, with no nucleotides in between the position of the 3' terminal nucleotide of the oligonucleotide and the position of the 3' end of the nucleotide. The hybridization of the oligonucleotide to the immediately 3' of the nucleotide of the target polynucleotide allows the incorporation of a nucleotide or a nucleotide analog (e.g., a ddNTP), in a template dependent manner, into the oligonucleotide at the position corresponding to the predetermined nucleotide of the target polynucleotide.

A "tag molecule" refers to a molecule covalently coupled to an oligonucleotide primer. An "anti-tag molecule" refers to a molecule which interacts with the tag molecule through specific binding. An anti-tag molecule useful in the invention may be further labeled with a member of a pair of interactive labels. The tag and anti-tag molecule pair allows the interaction of a labeled anti-tag molecule with an oligonucleotide primer which may comprise an incorporated labeled polynucleotide chain terminator. A tag molecule and its corresponding anti-tag molecule, according to the invention, can be members of a specific binding pair. It is not critical for either a tag molecule or an anti-tag molecule to be a specific member of a specific binding pair, so long as it permits the binding between the members of the specific binding pair.

As used herein, a "specific binding pair" refers to two different molecules, where one molecule has an area on the surface or in a cavity which specifically binds to and is thereby defined as complementary with a particular spatial and polar organization of the other molecule. The two molecules of a specific binding pair may also comprise complementary sequences and form the specific binding through base-pairing. A "specific binding pair", according to the invention, include, but are not limited to members of an immunological pair such as antigen-antibody, or an operator-repressor, nuclease-nucleotide, biotin-streptavidin, ligand-receptor pair, polynucleotide duplexes, IgG-protein A, DNA-DNA, DNA-RNA.

A specific binding pair can be used to separate an oligonucleotide primer or an oligonucleotide probe from a target polynucleotide when desired. The two different molecules in such a specific binding pair can also be referred to as a separation moiety and a target moiety. As used herein, a "separation moiety" is the molecule of a specific binding pair which is coupled to the oligonucleotide primer or the oligonucleotide probe. A "target moiety" refers to the other molecule of the specific binding pair which is optionally coupled to a solid support. "Separation", as used herein refers to physically separating one molecule from another molecule, for example, separating an oligonucleotide primer or an oligonucleotide primer/probe duplex from an unincorporated chain terminator or from an unhybridized oligonucleotide probe.

As used herein, a "solid support" refers to a porous or non-porous water insoluble material. The support can be hydrophilic or capable of being rendered hydrophilic and includes inorganic powders such as silica, magnesium sulfate and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, polyvinyl chloride, polyacrylamide, cross-linked dextran, agarose, polyacrylate, polyethylene, polypropylene, poly(4-methylbutene), polystyrene, polymethacrylate, polyethylene terephthalate, nylon, polyvinyl butyrate, etc.; either used by themselves or in conjunction with other materials; glass available as Bioglass, ceramics, metals, and the like. A "solid support" also include magnetic particle such as magnetic beads and such as disclosed in U.S. Pat. Nos. 5,898,071 and 5,705,628. Natural or synthetic assemblies such as liposomes, phospholipid vesicles and cells can also be employed.

Binding of a specific binding pair molecule to a support or surface may be accomplished by well-known techniques, commonly available in the literature. See, for example, "Immobilized Enzymes," Ichiro Chibata, Halsted Press, New York (1978) and Cuatrecasas, J. Biol. Chem., 245:3059 (1970). The surface can have any one of a number of shapes, such as strip, rod, particle or bead.

As used herein, "non-conventional nucleotide" refers to a) a nucleotide structure that is not one of the four conventional deoxynucleotides dATP, dCTP, dGTP, and dTTP recognized by and incorporated by a DNA polymerase, b) a synthetic nucleotide, c) a modified conventional nucleotide, or d) a ribonucleotide (since they are not normally recognized or incorporated by DNA polymerases) and modified forms of a ribonucleotide. Non-conventional nucleotides include but are not limited to those listed in Table 1, which are commercially available, for example, from New England Nuclear.

"Complementary" refers to the broad concept of sequence complementarity between regions of two polynucleotide strands or between two regions of the same polynucleotide strand. It is known that an adenine base of a first polynucleotide region is capable of forming specific hydrogen bonds ("base pairing") with a base of a second polynucleotide region which is antiparallel to the first region if the base is thymine or uracil. Similarly, it is known that a cytosine base of a first polynucleotide strand is capable of base pairing with a base of a second polynucleotide strand which is antiparallel to the first strand if the base is guanine. A first region of a polynucleotide is complementary to a second region of the same or a different polynucleotide if, when the two regions are arranged in an antiparallel fashion, at least one nucleotide of the first region is capable of base pairing with a base of the second region. A first polynucleotide that is 100% complementary to a second polynucleotide forms base pair at every nucleotide position. A first polynucleotide that is not 100% complementary (e.g., 90%, or 80% or 70% complementary) contains mismatched nucleotides at one or more nucleotide positions.

As used herein, a "detectable marker" or a "detectable label" refers to a molecule capable of generating a detectable signal. A "detectable marker" may be detected directly or detectable through a specific binding reaction that generates a detectable signal. The label can be isotopic or non-isotopic, usually non-isotopic, and can be a catalyst, such as an enzyme (also referred to as an enzyme label), a polynucleotide coding for a catalyst, promoter, dye, fluorescent molecule (also referred to as a fluorescent label), chemiluminescer (also referred to as a chemiluminescent label), coenzyme, enzyme substrate, radioactive group (also referred to as a radiolabel), a small organic molecule, amplifiable polynucleotide sequence, a particle such as latex or carbon particle, metal sol, crystallite, liposome, cell, etc., which may or may not be further labeled with a dye (also referred to as a colorimetric label), catalyst or other detectable group, and the like. The label may be a directly detectable label or may be a member of a signal generating system, and thus can generate a detectable signal in context with other members of the signal generating system, e.g., a biotin-avidin signal generation system. The label can be bound directly to a nucleotide or a polynucleotide sequence or indirectly via a linker.

The preferred labels, according to the invention, are members of a pair of interactive labels. The members of a pair of "interactive labels" generates a detectable signal when brought in close proximity. The signals generated is preferably detectable by visual examination methods well known in the art, preferably by a fluorescence resonance energy transfer assay (FRET) (Stryer et al., 1978, Ann. Rev. Biochem., 47:819; Selvin, 1995, Methods Enzymol., 246:300).

First and second members of a pair of interactive labels may be a donor and an acceptor, a receptor and a quencher, or vice versa. As used herein, the term "donor" refers to a fluorophore which absorbs at a first wavelength and emits at a second, longer wavelength. The term "acceptor" refers to a fluorophore, chromophore or quencher with an absorption spectrum which overlaps the donor's emission spectrum and is able to absorb some or most of the emitted energy from the donor when it is near the donor group (typically between 1–100 nm). If the acceptor is a fluorophore capable of exhibiting FRET, it then re-emits at a third, still longer wavelength; if it is a chromophore or quencher, then it releases the energy absorbed from the donor without emitting a photon. Although the acceptor's absorption spectrum overlaps the donor's emission spectrum when the two groups are in proximity, this need not be the case for the spectra of the molecules when free in solution. Acceptors thus include fluorophores, chromophores or quenchers that, following attachment to either a chain terminator or to an anti-tag molecule, show alterations in absorption spectrum which permit the group to exhibit either FRET or quenching when placed in proximity to the donor through the binding interactions of the anti-tag molecule and a tag molecule comprising the chain terminator.

As used herein, a "reporter molecule" is a molecule capable of generating a fluorescence signal. A "quencher molecule" is a molecule capable of absorbing the fluorescence energy of an excited reporter molecule, thereby quenching the fluorescence signal that would otherwise be released from the excited reporter molecule. In order for a quencher molecule to quench an excited fluorophore, the quencher molecule must be within a minimum quenching distance of the excited reporter molecule at some time prior to the reporter molecule releasing the stored fluorescence energy.

According the invention, a pair of interactive labels may comprise more than one second member, each second member can interact with the same first member of the pair of interactive labels and generate a distinguishable signal transfer which is indicative of the identity of each of the second member.

As used herein, references to "fluorescence" or "fluorescent groups" or "fluorophores" include luminescence and luminescent groups, respectively.

As used herein, the term "hybridization" is used in reference to the pairing of complementary polynucleotide strands. Hybridization and the strength of hybridization (i.e., the strength of the association between polynucleotide strands) is impacted by many factors well known in the art including the degree of complementarity between the polynucleotides, stringency of the conditions involved affected by such conditions as the concentration of salts, the Tm (melting temperature) of the formed hybrid, the presence of other components (e.g., the presence or absence of polyethylene glycol), the molarity of the hybridizing strands and the G:C content of the polynucleotide strands.

As used herein, the term "stringency" is used in reference to the conditions of temperature, ionic strength, and the presence of other compounds, under which polynucleotide hybridizations are conducted. With "high stringency" conditions, polynucleotide pairing will occur only between polynucleotide fragments that have a high frequency of complementary base sequences. Thus, conditions of "weak" or "low" stringency are often required when it is desired that polynucleotides which are not completely complementary to one another be hybridized or annealed together. The art knows well that numerous equivalent conditions can be employed to comprise high or low stringency conditions.

As used herein, "high stringency conditions" refer to temperature and ionic condition used during polynucleotide hybridization and/or washing. The extent of "high stringency" is nucleotide sequence dependent and also depends upon the various components present during hybridization. Generally, highly stringent conditions are selected to be about 5 to 20 degrees C. lower than the thermal melting point (Tm) for the specific sequence at a defined ionic strength and pH. The Tm is the temperature defined by the following equation: $T_m = 69.3 + 0.41 \times (G+C)\% - 650/L$, wherein L is the length of the probe in nucleotides. "High stringency conditions", as used herein, refer to a washing procedure including the incubation of two or more hybridized polynucleotides in an aqueous solution containing 0.1×SSC and 0.2% SDS, at room temperature for 2–60 minutes, followed by incubation in a solution containing 0.1×SSC at room temperature for 2–60 minutes. "High stringency conditions" are known to those of skill in the art, and may be found in, for example, Maniatis et al., 1982, *Molecular Cloning*, Cold Spring Harbor Laboratory and Schena, ibid.

As used herein, "low stringency conditions" refer to a washing procedure including the incubation of two or more hybridized polynucleotides in an aqueous solution comprising 1×SSC and 0.2% SDS at room temperature for 2–60 minutes.

As used herein, the term "Tm" is used in reference to the "melting temperature". The melting temperature is the temperature at which 50% of a population of double-stranded polynucleotide molecules becomes dissociated into single strands. The equation for calculating the Tm of polynucleotides is well-known in the art. The Tm of a hybrid polynucleotide is often estimated using a formula adopted from hybridization assays in 1 M salt, and commonly used for calculating Tm for PCR primers: {(number of A+T)×2° C.+(number of G+C)×4° C.}; see, for example, C. R. Newton et al. PCR, 2nd Ed., Springer-Verlag (New York: 1997), p. 24. This formula was found to be inaccurate for primers longer that 20 nucleotides. Other more sophisticated computations exist in the art which take structural as well as sequence characteristics into account for the calculation of Tm. A calculated Tm is merely an estimate; the optimum temperature is commonly determined empirically.

"Polynucleotide chain terminator", or "chain terminator", or "terminator" means any nucleotide that when incorporated into a primer extension product prevents the further extension of such primer extension product. One requirement of a nucleotide terminator is that when the nucleotide terminator includes a ribofuranose sugar portion, the 3'-position must not have a hydroxy group capable of being subsequently used by a polymerase to incorporate additional nucleotides, e.g., dideoxyadenosine triphosphate (ddATP), dideoxycytosine triphosphate (ddCTP), dideoxyguanosine triphosphate (ddGTP), dideoxythymidine triphosphate (ddTTP), or dideoxyuridine triphosphate (ddUTP). Alternatively, a ribofuranose analog could be used, such as arabinose. Exemplary nucleotide terminators include 2',3'-dideoxy-β-D-ribofuranosyl, β-D-arabinofuranosyl, 3'-deoxy-β-D-arabinofuranosyl, 3'-amino-2',3'-dideoxy-β-D-ribofuranosyl, and 2',3'-dideoxy-3'-fluoro-β-D-ribofuranosyl (Chidgeavadze). Nucleotide terminators also include reversible nucleotide terminators (Metzker) and acyclic terminators.

"Primer extension reaction" or "chain elongation reaction" means a reaction between a target-primer hybrid and a nucleotide which results in the addition of the nucleotide to a 3'-end of the primer such that the incorporated nucleotide is complementary to the corresponding nucleotide of the target polynucleotide. Primer extension reagents typically include (i) a polymerase enzyme; (ii) a buffer; and (iii) one or more extendible nucleotides. Both conventional sequencing and mini-sequencing act as primer extension reactions until a nucleotide terminator is incorporated. Mini-sequencing reagents, according to the present invention may comprise an extendible nucleotide.

As used herein, "polymerase chain reaction" or "PCR" refers to an in vitro method for amplifying a specific polynucleotide template sequence. The PCR reaction involves a repetitive series of temperature cycles and is typically performed in a volume of 50–100 μl. The reaction mix comprises dNTPs (each of the four deoxynucleotides dATP, dCTP, dGTP, and dTTP), primers, buffers, DNA polymerase, and polynucleotide template. One PCR reaction may consist of 5 to 100 "cycles" of denaturation and synthesis of a polynucleotide molecule.

As used herein, "polynucleotide polymerase" refers to an enzyme that catalyzes the polymerization of nucleotide. Generally, the enzyme will initiate synthesis at the 3'-end of the primer annealed to a polynucleotide template sequence, and will proceed toward the 5' terminal of the template strand. "DNA polymerase" catalyzes the polymerization of deoxynucleotides. Useful DNA polymerases include, but are not limited to, Pyrococcus furiosus (Pfu) DNA polymerase (Lundberg et al., 1991, Gene, 108:1; U.S. Pat. No. 5,556,772, incorporated herein by reference), Thermus thermophilus (Tth) DNA polymerase (Myers and Gelfand 1991, Biochemistry 30:7661), Bacillus stearothermophilus DNA polymerase (Stenesh and McGowan, 1977, Biochim Biophys Acta 475:32), Thermococcus litoralis (Tli) DNA polymerase (also referred to as Vent DNA polymerase, Cariello et al., 1991, Polynucleotides Res, 19: 4193), Thermotoga maritima (Tma) DNA polymerase (Diaz and Sabino, 1998 Braz J. Med. Res, 31:1239), Pyrococcus kodakaraensis KOD DNA polymerase (Takagi et al., 1997, Appl. Environ. Microbiol. 63:4504), JDF-3 DNA polymerase (Patent application WO 0132887), and Pyrococcus GB-D (PGB-D) DNA polymerase (Juncosa-Ginesta et al., 1994, Biotechniques, 16:820). The polymerase activity of any of the above enzyme can be defined by means well known in the art. One unit of DNA polymerase activity, according to the subject invention, is defined as the amount of enzyme which catalyzes the incorporation of 10 nmoles of total dNTPs into polymeric form in 30 minutes at optimal temperature.

DNA polymerases used in the present invention are preferred to have reduced discrimination against non-conventional nucleotides.

As used herein, "discrimination" refers to the tendency of DNA polymerase to not carry out the incorporation of non-conventional nucleotides into the nascent DNA polymer. DNA polymerase has the ability to sense nucleotide structure, including but not limited to nucleotide complementarity, and structural features of the sugar and heterocyclic base, thereby allowing DNA polymerase to preferentially utilize conventional deoxynucleotides rather than non-conventional nucleotides for incorporation into a nascent polymer. DNA polymerase strongly prefers to incorporate the conventional deoxynucleotides dATP, dCTP, dGTP and dTTP into DNA polymers; the polymerase is unlikely to progress with an unconventional nucleotide in its binding pocket.

As used herein, "reduced discrimination" refers to a reduction in the tendency of a DNA polymerase to exclude non-conventional nucleotides from, or to not incorporate non-conventional nucleotides into, a nascent DNA polymer as compared to the natural tendency of the DNA polymerase. The preference of DNA polymerase to incorporate the conventional deoxynucleotides dATP, dCTP, dGTP and TTP rather than non-conventional nucleotides into DNA polymers is thereby reduced compared to the natural level of preference, such that non-conventional nucleotides are more readily incorporated into DNA polymers by DNA polymerase. Discrimination may be quantitated by measuring the concentration of a non-conventional nucleotide necessary to inhibit the incorporation of the corresponding conventional nucleotide by 50%. This concentration is referred to herein as the "$I_{50\%}$" for a non-conventional nucleotide. Discrimination against a given non-conventional nucleotide is "reduced" if the $I_{50\%}$ for that non-conventional nucleotide is reduced by at least two fold relative to an identical assay containing, in place of the mutant DNA polymerase, a parental DNA polymerase. Alternatively, reduced discrimination may be quantitated by determining the amount of a non-conventional nucleotide (for example, a dideoxynucleotide, ribonucleotide, or cordycepin) necessary in a reaction with a mutant enzyme to generate a sequencing ladder comparable to a sequencing ladder produced using the wild-type or parental enzyme. For this type of assay, a constant amount of dNTPs and varying amounts of non-conventional nucleotides are used to generate a sequencing ladder with both the wild-type or parental enzyme and the mutant enzyme (for ribonucleotides, a sequencing ladder is generated by alkalai cleavage of the polymerization products). The sequencing ladders are then examined in the range of 1 to 400 bases from the primer. For details of this type of assay, see Gardner & Jack, 1999, supra. A mutant exhibits reduced discrimination of it requires at least two-fold less, five-fold less, ten-fold less, or an even greater fold smaller in the amount of the non-conventional nucleotide to produce a sequencing ladder comparable (with respect to the length of extension products generated) to that generated by the wild-type or parental enzyme using a given amount of nucleotide analog.

As used herein, "3' to 5' exonuclease deficient" or "3' to 5' exo$^-$" refers to an enzyme that substantially lacks the ability to remove incorporated nucleotides from the 3' terminal of a DNA polymer. DNA polymerase exonuclease activities, such as the 3' to 5' exonuclease activity exemplified by members of the Family B polymerases, can be lost through mutation, yielding an exonuclease-deficient polymerase. As used herein, a DNA polymerase that is deficient in 3' to 5' exonuclease activity substantially lacks 3' to 5' exonuclease activity. "Substantially lacks" encompasses a complete lack of activity, 0.03%, 0.05%, 0.1%, 1%, 5%, 10%, 20% or even up to 50% of the exonuclease activity relative to the parental enzyme.

The term "sample" as used herein is used in its broadest sense. A sample may comprise a cell, chromosomes isolated from a cell (e.g., a spread of metaphase chromosomes), genomic DNA, RNA, cDNA and the like.

A "single nucleotide polymorphism" or SNP, as used herein, is a variation from the most frequently occurring base at a particular polynucleotide position.

The invention relates to improved methods and assays for identifying a nucleotide at a predetermined location on a target polynucleotide. A nucleotide is identified by incorporating into an oligonucleotide primer a labeled terminator that base pairs with the nucleotide having identity to be determined. The oligonucleotide primer comprises a first sequence which is complementary to and hybridize to the target polynucleotide.

In a preferred embodiment, the oligonucleotide primer also comprises a second sequence which does not hybridize to the target polynucleotide. In this embodiment, a labeled oligonucleotide probe comprising a third sequence hybridizes to the oligonucleotide primer after the incorporation of the labeled terminator and cause the generation of a signal by energy transfer (e.g., FRET). The signal indicates the identity of the nucleotide to be determined. The improvement relates to the use of an oligonucleotide primer with a second sequence, preferably at the 5' terminal of the oligonucleotide primer, and a labeled oligonucleotide probe which is capable of hybridizing to the second sequence of the oligonucleotide primer. By employing the second sequence on the oligonucleotide primer and the oligonucleotide probe, one can design a common second sequence for a number of different oligonucleotide primers and therefore use a common oligonucleotide probe to hybridize to the common second sequence. The label on the probe can interact with the label on an incorporated polynucleotide chain terminator to generate an energy transfer. The oligonucleotide primer itself needs not to be labeled. Therefore the requirement for synthesizing an expensive, fluorescently labeled primer for each target polynucleotide locus being examined is eliminated.

The subject methods and assays include incubating a target polynucleotide in a reaction mixture comprising an oligonucleotide primer which hybridizes to the target polynucleotide immediately 3' of the nucleotide, an oligonucleotide probe which hybridizes to the oligonucleotide primer and labeled with a first member of a pair of interactive labels, a polynucleotide chain terminator labeled with a second member of the pair of interactive labels, where the incubating permits the polynucleotide chain terminator to be incorporated into said oligonucleotide primer, and allows the oligonucleotide probe to hybridize to the oligonucleotide primer to permit the pair of interactive labels to generate a signal by fluorescent resonance energy transfer.

The subject methods and assays also include: (a) incubating a target polynucleotide in a reaction mixture comprising an oligonucleotide primer which hybridizes to the target polynucleotide immediately 3' of the nucleotide and a polynucleotide chain terminator labeled with a second member of a pair of interactive labels, where the incubating permits the polynucleotide chain terminator to be incorporated into the oligonucleotide primer; and (b) incubating the oligonucleotide primer comprising the second member of the pair of interactive labels with the oligonucleotide probe labeled with a first member of the pair of interactive labels, such that formation of a hybrid between the oligonucleotide probe and the primer permits said pair of interactive labels to a generate a signal by fluorescent resonance energy transfer.

In the reaction mixture, the target polynucleotide and the oligonucleotide primer forms a duplex (double stranded polynucleotide). The oligonucleotide primer hybridizes to the target polynucleotide immediately 3' of the nucleotide at a predetermined position, thereby forcing the next nucleotide to be incorporated into the oligonucleotide primer to base pair with the nucleotide to be identified. Preferably, the target polynucleotide for analysis is from a genomic or cDNA preparation. The step of duplex formation may take place by polynucleotide hybridization or may take place concomitantly with a reaction that generates a duplex polynucleotide. For example, a duplex between an oligonucleotide primer and a target polynucleotide for analysis may be formed during the process of a restriction endonuclease digestion, e.g., the recessed 3' terminal of the digestion product can serve as the oligonucleotide primer for extension. The oligonucleotide primer may or may not be perfectly complementary to the target polynucleotide for analysis. Thus, the duplex may contain one or more mismatches, provided that the mismatches do not significantly interfere with the ability of a DNA polymerase to extend the oligonucleotide primer or interfere with the ability of the 3' terminus nucleotide of the oligonucleotide primer to hybridize immediately 3' of the nucleotide at the predetermined location on the target polynucleotide for analysis.

The target polynucleotide for analysis serves as a template for the labeled terminators that are incorporated into the elongating chain comprising the oligonucleotide primer. The target polynucleotide for analysis may be produced by any of a variety of polynucleotide preparation techniques generally known to those of ordinary skill in the art of molecular biology. Examples of such preparation techniques include, direct extraction of polynucleotides, cDNA formation, polynucleotide amplification (e.g., the polymerase chain reaction), and the like.

Subsequent to the formation of the duplex polynucleotide molecule, the oligonucleotide primer is extended by one nucleotide in a DNA polymerase catalyzed polynucleotide chain extension reaction. The single incorporated nucleotide is complementary to the nucleotide to be determined at the predetermined location. The extension reaction takes place in a reaction extension reaction mixture comprising at least one labeled terminator. The extension reaction mixture also comprises other reagents necessary for primer extension such as a DNA polymerase, a buffer suitable for the DNA polymerase, and the like. In preferred embodiments of the invention, four polynucleotide chain terminators are used in the reaction, each of the terminators labeled with a different second member of a pair of interactive labels. Therefore, a first member of a pair of interactive labels may have more than one second member. The second members used in the same reaction mixture to interact with the same first member of the pair of interactive labels are selected so as to not significantly interfere with the detection of the each other. In preferred embodiments of the invention, the detectable labels are fluorescent dyes that are spectrally resolvable from one another. As naturally occurring polynucleotides have one of four possible nucleotide (e.g., A, T, G and C) at a predetermined position, a set of four labeled terminators is sufficient to determine the identity of a nucleotide at a given location on a target polynucleotide. Less than four unlabeled terminators may be employed when the nucleotide at the predetermined location is known not to be of a certain base, thereby obviating the need to test for the presence of that nucleotide.

The different labeled polynucleotide chain terminators present in a reaction mixture are labeled with different second labels that may readily be distinguished from one another, upon their interaction with the first member of the pair of interactive labels. The second member on a given labeled terminator is correlated with the chemical structure (e.g., identity) of the nucleotide of the terminator. Thus by detecting and identifying the signal transfer generated from the label, the identity of the base may be ascertained.

In another embodiment of the invention, the oligonucleotide primer is covalently coupled to a tag molecule. Preferably, the tag molecule is a first member of a specific binding pair (e.g., biotin or a ligand). A labeled chain terminator (e.g., labeled with a second member of a pair of interactive labels) is incorporated into the oligonucleotide primer by chain elongation. In this embodiment, an anti-tag molecule comprising the second corresponding member of the specific binding pair (e.g., streptavidin or a receptor for the ligand) is labeled with a first member of the pair of interactive labels. The labeled anti-tag molecule interacts with the tag molecule through the specific binding between the members of the specific binding pair to generate a signal by energy transfer (e.g., FRET).

Polynucleotides or Oligonucleotide Probes and Primers

A polynucleotide or an oligonucleotide can be obtained by biological synthesis or by chemical synthesis. For short sequences (up to about 100 nucleotides) chemical synthesis is frequently more economical as compared to biological synthesis. For longer sequences standard replication methods employed in molecular biology can be used such as the use of M13 for single stranded DNA as described by Messing, 1983, *Methods Enzymol.* 101: 20–78. Chemical methods of polynucleotide or oligonucleotide synthesis include phosphotriester and phosphodiester methods (Narang, et al., Meth. Enzymol. (1979) 68:90) and synthesis on a support (Beaucage, et al., Tetrahedron Letters. (1981) 22:1859–1862) as well as phosphoramidate technique, Caruthers, M. H., et al., Methods in Enzymology (1988) 154:287–314 (1988), and others described in "Synthesis and Applications of DNA and RNA," S. A. Narang, editor, Academic Press, New York, 1987, and the references contained therein.

Oligonucleotide probes and primers can be synthesized by any method described above and other methods known in the art. The primer and probe used for identifying a nucleotide at a predetermined position of a target polynucleotide can be designed to have different lengths, so that by controlling the annealing temperature, the reaction can be driven towards more primer annealing to the target polynucleotide or annealing of primer to the probe which creates a detectable signal. Preferably, the 3' terminal of the probe is blocked by adding a phosphate or an amine group, or the like to prevent chain elongation from the 3' terminal of the probe.

In one embodiment of the invention, the oligonucleotide primer comprises a first sequence which hybridizes to the target polynucleotide template. In a preferred embodiment, the oligonucleotide primer comprises a first sequence, which hybridizes to the target polynucleotide template, and a second sequence which does not hybridize to the target polynucleotide template. The first sequence, which hybridizes to the target template, may be at least 70% (e.g., at least 80% or at least 90% or more) complementary to the target template and comprises 10 to 100 nucleotides in length, preferably 15 to 50 nucleotides in length, more preferably 17–30 nucleotides in length. The second sequence, which does not hybridize to the target template, may be less than 50% (e.g., less than 40%, or 30%, or 20% or 10%) complementary to the target template and comprises 10 to 50 nucleotides in length, preferably 20–35 nucleotides in length. The second sequence may be any sequence so long as it does not hybridize to the target template and does not interfere with the hybridization of the first sequence to the target template.

The second sequence, which does not hybridize to the target template, may be located at any position of the primer so long as it does not interfere with the annealing of the primer to the target template for primer extension. In one embodiment, the second sequence is located in the "middle" of the primer, preferably, at least 10 nucleotides (e.g., at least 15 nucleotides, or at least 20 nucleotides, or 30 nucleotides or more) from the 3' terminus of the primer, or up to 1 nucleotide away from the 5' terminus of the primer. In another embodiment, the second sequence is located at the 5' terminal of the primer.

The second sequence, according to the invention, may be a universal sequence (i.e., a common sequence) which is identical for a number of primers. Each of the number of primers also comprises its unique first sequence which hybridizes to its target polynucleotide template. The universal sequence does not hybridize to the target polynucleotide templates, but serves to provide a common sequence from which a universal oligonucleotide probe may be designed (i.e., a common oligonucleotide probe complementary to the universal sequence). Therefore, the use of the universal sequence as the second sequence on a number of primers avoids the laborious and costly design of a specific oligonucleotide probe for each primer used in the invention.

Nucleotides And Polynucleotide Chain Terminators

Polynucleotide chain terminators can be labeled (e.g., physically joined) to a detectable label. The linkage to the detectable label is at a site or sites on that terminator that do not prevent the incorporation of the terminator into a tag molecule (e.g., an oligonucleotide primer) in a reaction catalyzed by a DNA polymerase. The detectable label serves to (1) signal the incorporation of the terminator into a polynucleotide and (2) to indicate the structure of the nucleotide moiety of the terminator that has been incorporated by way of a predetermined correlation between the signal produced through the interaction between the tag molecule and its corresponding anti-tag molecule.

"Nucleotide Analog" refers to a nucleotide in which the pentose sugar and/or one or more of the phosphate esters is replaced with its respective analog. Exemplary pentose sugar analogs are those previously described in conjunction with nucleoside analogs. Exemplary phosphate ester analogs include, but are not limited to, alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, etc., including any associated counterions, if present.

Also included within the definition of "nucleotide analog" are nucleobase monomers which can be polymerized into polynucleotide analogs in which the DNA/RNA phosphate ester and/or sugar phosphate ester backbone is replaced with a different type of linkage.

Useful chain terminators include, but are not limited to, conventional dideoxynucleotide chain terminator (e.g., ddATP, ddTTP, ddCTP, and ddGTP) and non-conventional dideoxynucleotide analogs (Table 1).

TABLE 1

Non - Conventional Dideoxynucleotide Analogs

| Fluorescein Labeled | Fluorophore Labeled |
| --- | --- |
| Fluorescein - 12 - ddCTP | Eosin - 6 - ddCTP |
| Fluorescein - 12 - ddUTP | Coumarin - 5 - ddUTP |
| Fluorescein - 12 - ddATP | Tetramethylrhodamine - 6 - ddUTP |
| Fluorescein - 12 - ddGTP | Texas Red - 5 - ddATP |
| Fluorescein - N6 - ddATP | LISSAMINETM - rhodamine - 5 - ddGTP |
| FAM Labeled | TAMRA Labeled |
| FAM - ddUTP | TAMRA - ddUTP |
| FAM - ddCTP | TAMRA - ddCTP |
| FAM - ddATP | TAMRA - ddATP |
| FAM - ddGTP | TAMRA - ddGTP |
| ROX Labeled | JOE Labeled |
| ROX - ddUTP | JOE - ddUTP |
| ROX - ddCTP | JOE - ddCTP |
| ROX - ddATP | JOE - ddATP |
| ROX - ddGTP | JOE - ddGTP |
| R6G Labeled | R110 Labeled |
| R6G - ddUTP | R110 - ddUTP |
| R6G - ddCTP | R110 - ddCTP |
| R6G - ddATP | R110 - ddATP |
| R6G - ddGTP | R110 - ddGTP |
| BIOTIN Labeled | DNP Labeled |
| Biotin - N6 - ATP | DNP - N6 - ddATP |

Up to four different chain terminators, i.e., one, two, three, or four may be used for the subject composition and method of the invention. Each chain terminator is labeled with a different label and emits a different signal when excited or quenched by the corresponding interactive label on the probe.

In some embodiments of the invention, a conventional deoxynucleotide is labeled with a member of a pair of interactive labels in similar manner described above. The labeled deoxynucleotide may be used in combination with an unlabeled chain terminator, so that the deoxynucleotide is incorporated into the oligonucleotide primer at the position corresponding to the predetermined position and the chain terminator terminates the primer extension at 3' nucleotide position of the incorporated deoxynucleotide.

In a preferred embodiment, the reaction mixture comprises a labeled conventional deoxynucleotide and four unlabeled chain terminators. Up to four such reactions may be performed (i.e., each comprising a labeled deoxynucleotide) for the identification of a predetermined nucleotide of a target polynucleotide.

Fluorescent Dyes

Fluorescent dye-labeled chain terminators and polynucleotide probes can be purchased from commercial sources. Labeled polynucleotides probes can also be prepared by any of a number of approaches. For example, unlabeled polynucleotides can be prepared by excision, transcription or chemical synthesis. Labeling of the polynucleotide probe with a fluorescent dye can be done internally or by end labeling using methods well known in the art (see, for example, Ju et al., Proc Nat Acad Sci 92:4347–4351, 1995; Nelson et al. Polynucleotides Res 20:6253–6259, 1992 which are incorporated by reference).

Preferably, a chain terminator, an oligonucleotide probe and an anti-tag molecule is labeled with a fluorescent dye. Fluorescent dyes useful as detectable labels are well known to those skilled in the art and numerous examples can be found in the *Handbook of Fluoresdent Probes and Research Chemicals* 6th Edition, Richard Haugland, Molecular Probes, Inc., 1996 (ISBN 0-9652240-0-7). The detectable label may be joined directly to the terminator or anti-tag molecule, or it may be joined through a linker. Examples of suitable linkers are described in U.S. Pat. No. 5,770,716. Preferably, the detectable label is joined to the nucleotide moiety of the terminator so as not to prevent the incorporation of the labeled terminator in a DNA polymerase catalyzed reaction. Also preferably, the detectable label is joined to the nucleotide moiety of the anti-tag molecule so as not to prevent the interaction between the anti-tag molecule and its corresponding tag molecule (e.g., during a hybridization reaction). The labels may be any fluorescent label or fluorophore that does not interfere with the ability of the oligonucleotide probe to interact with the oligonucleotide primer comprising a labeled polynucleotide chain terminator, and is able to show or fluorescence resonance energy transfer with the corresponding label on the polynucleotide chain terminator. Detectable labels may be compounds or elements detectable by techniques other than, or in addition to, fluorescence. Such additional labels include radioisotopes, chemiluminescent compounds, spin labels, immunologically detectable haptens, and the like.

Preferably, fluorescent dyes are selected for compatibility with detection on an automated DNA sequencer and thus should be spectrally resolvable and not significantly interfere with electrophoretic analysis. In general, fluorescent dye labeled terminators suitable for DNA sequencing by the subject methods are suitable for use in the subject methods. Examples of suitable fluorescent dyes for use as detectable labels on labeled terminators can be found in among other places, U.S. Pat. Nos. 5,750,409; 5,366,860; 5,231,191; 5,840,999; 5,847,162; 4,439,356; 4,481,136; 5,188,934; 5,654,442; 5,840,999; 5,750,409; 5,066,580; 5,750,409; 5,366,860; 5,231,191; 5,840,999; 5,847,162; 5,486,616; 5,569,587; 5,569,766; 5,627,027; 5,321,130; 5,410,030; 5,436,134; 5,534,416; 5,582,977; 5,658,751; 5,656,449; 5,863,753; PCT Publications WO 97/36960; 99/27020; 99/16832; European Patent EP 0 050 684; Sauer et al, 1995, J. Fluorescence 5:247–261; Lee et al., 1992, Nucl. Acids Res. 20:2471–2483; and Tu et al., 1998, Nucl. Acids Res. 26:2797–2802.

The oligonucleotide probe may be fluorescently labeled at any suitable position. For instance, the fluorescent group may be placed on or adjacent to the 5' terminal of the oligonucleotide probe. In other instances, the fluorescent group may be placed on or adjacent to the 3' terminal of the oligonucleotide probe.

Alternatively, the fluorescent group may be placed on or adjacent to the 3' or 5' end of a nucleotide within the oligonucleotide probe, for instance by incorporation of a fluorescent nucleotide derivative, modification of a nucleotide or substitution of a nucleotide by a fluorescent molecule. For example, tetramethylrhodamine (TAMRA) can be introduced into the oligonucleotide probe by incorporating the modified deoxy-thymidine phosphoramidite (5'-Dimethoxytrityloxy-5-[N-((tetramethyl-odaminyl)-aminohexyl)-3-acryimido]-2'-deoxy-thymidine-3'-[(2-cyanoethyl)-(N,N-diisopropyl)]-phosphoramidite). Fluorescein may be incorporated in an analogous way with: 5'-Dimethoxytrityloxy-5-[N -((3',6'-dipivaloylfluoresceinyl)-aminohexyl)-3-acryimido]-2'-deoxy-thymidine-3'-[(2-cyanoethyl)-(N,N-diisopropyl)]-phosphoramidite. The DABCYL group may also be incorporated using 5'-Dimethoxytrityloxy-5-[N-((4-(dimethylamino)azobenzene) -aminohexyl)-3-acryimido]-2'-deoxy-thymidine-3'-[(2-cyanoethyl)-(N,N -diisopropyl)]-phosph-oramidite. More generally, a free amino group may be reacted with the active ester of any dye; such an amino group may be introduced by the inclusion of the modified thymidine 5'-Dimethoxytrityl-5-[N-(trifluoroacetylaminohexyl)-3-acrylimido]-2'-deoxy-thymidine, 3'-[(2-cyanoethyl)-(N,N-diisopropyl)]-phosphoramidite. Preferably, the incorporation of a modified base allows for normal base pairing. One skilled in the art should understand that thymidine in the above analogs may be substituted with other nucleotide (e.g., Guanosine, Adenosine, or Cytidine).

The oligonucleotide probes and polynucleotide chain terminators contain primary and secondary amines, hydroxyl, nitro and carbonyl groups. Methods that can be used to make fluorescent oligonucleotide probes and chain terminators are described below.

A number of chemical reactions can be applied to the fluorescent labeling of amines including but not limited to the following, where the fluorescent dye is conjugated to the indicated reactive group:

TABLE 2

| Functional Group | Reaction | Product |
| --- | --- | --- |
| Amine | dye - isothiocyanates | Thiourea |
| Amine | dye - succinimidyl ester | Carboxamide |
| Amine | dye - sulfonyl chloride | Sulphonamide |
| Amine | dye - aldehyde | Alkylamine |

Oligonucleotide probes or chain terminators containing amine groups that are appropriate for the introduction of fluorescent dyes include but are not limited to those listed in Table 2.

A number of chemical reactions can be applied to the fluorescent labeling of ketone groups including but not limited to the following, where the fluorescent dye is conjugated to the indicated reactive group:

TABLE 3

| Functional Group | Reaction | Product |
| --- | --- | --- |
| Ketone | dye - hydrazides | Hydrazones |
| Ketone | dye - semicarbazides | Hydrazones |
| Ketone | dye - carbohydrazides | Hydrazones |
| Ketone | dye - amines | Alkylamine |

Oligonucleotide probes or chain terminators containing ketone groups that are appropriate for the introduction of fluorescent dyes include but are not limited to those listed in Table 3.

A number of chemical reactions can be applied to the fluorescent labeling of aldehyde groups including but not limited to the following, where the fluorescent dye is conjugated to the indicated reactive group:

TABLE 4

| Functional Group | Reaction | Product |
| --- | --- | --- |
| Aldehyde | dye - hydrazides | Hydrazones |
| Aldehyde | dye - semicarbazides | Hydrazones |
| Aldehyde | dye - carbohydrazides | Hydrazones |
| Aldehyde | dye - amines | Alkylamine |

Oligonucleotide probes or chain terminators containing aldehyde groups that are appropriate for the introduction of fluorescent dyes include but are not limited to those listed in Table 4.

Dehydrobutyrene and dehydroalanine moieties have characteristic reactions that can be utilized to introduce fluorophores, as illustrated but not limited to the following, where the fluorescent dye is conjugated to the indicated reactive group:

TABLE 5

| Functional Group | Reaction | Product |
| --- | --- | --- |
| Dehydrobutyrine | dye - sulphydryl | Methyl lanthionine |
| Dehydroalanine | dye - sulphydryl | Lanthionine |

Oligonucleotide probes or chain terminators containing aldehyde groups that are appropriate for the introduction of fluorescent dyes include but are not limited to those listed in Table 5.

Other useful fluorophores (in addition to those listed in Tables 1–4) include, but are not limited to: TEXAS RED™ (Sulforhodamine 101-α-bungarotoxin), LISSAMINE™ rhodamine B (1,2-dihexadecanoyl-sn-glycero-3-phosohoethanolamine), OREGON GREEN™ 488 (2',7'-difluorofluorescein), carboxyrhodol and carboxyrhodamine, OREGON GREEN™ 500 ($C_{20}H_{10}F_2O_8S$), 6-JOE (6-carboxy-4',5'-dichloro-2',7'-dimethyoxyfluorescein, eosin F3S (6-carobxymethylthio-2',4',5',7'-tetrabromo-trifluorofluorescein), CASCADE BLUE™ (ethylenediamine trisodium), aminomethylcoumarin (AMC), pyrenes, dansyl chloride (5-dimethylaminonaphthalene -1-sulfonyl chloride) and other napththalenes, PyMPO, ITC (1-(3-isothiocyanatophenyl)-4-(5-(4-methoxyphenyl)oxazol-2-yl) pyridinium bromide).

Members of Pair of Interactive Labels

A pair of interactive labels comprises a first and a second member. A first member may have more than one, e.g., two, three, or four different second members. The members may be a donor and an acceptor pair for generating detectable signal transfer. It is not critical which member of the interactive labels is the donor or the acceptor. In preferred embodiment, the first member which is used to label the oligonucleotide probe of the invention is a donor and the second member which is used to label the polynucleotide chain terminator is the acceptor. The stimulation of the acceptor by the donor, when brought to close proximity, generates a detectable signal transfer. When more than one terminator is used in the reaction mixture and each terminator is labeled with a different second member (e.g., a different acceptor), the same first member (e.g., the donor) will interact with each second member (e.g., acceptor) and cause a different signal transfer to be detected.

Contact between the two members (e.g., donor and acceptor) in a pair of interactive labels may occur in solution (e.g., a test tube, dish or well of a microtitre plate) or, alternatively, either the oligonucleotide probe molecule or the oligonucleotide primer comprising an incorporated chain terminator may be adhered to a solid support (e.g., an affinity gel, matrix, or column) by covalent or non-covalent linkages using methods known in the art. The support bound primer comprising the chain terminator or oligonucleotide probe molecule is then mixed with a solution containing the other compounds of the reaction mixture.

When the oligonucleotide probe and the oligonucleotide comprising the chain terminator are mixed, they can form a complex which brings the first and second members of a pair of interactive labels into proximity. The "fluorescence" of, or light emitted from, the complex formed between the oligonucleotide probe molecule and the polynucleotide chain terminator on the elongating chain is altered by fluorescence resonance energy transfer (FRET). "FRET" is a distance-dependent interaction between the electronic exited states of two dye molecules in which excitation is transferred from a donor molecule to an acceptor molecule. FRET is dependent on the inverse sixth power of the intermolecular separation, making it useful over distances comparable to the dimensions of biological macromolecules and obtainable in the complexes formed between the oligonucleotide probe molecules and polynucleotide chain terminator molecules in the method of this invention. In most embodiments, the donor and acceptor dyes for FRET are different, in which case FRET can be detected by the appearance of sensitized fluorescence of the acceptor. When the donor and acceptor are the same, FRET is detected by the resulting fluorescence depolarization.

Since a common labeled oligonucleotide probe may be used to detect four different labeled chain terminators, if the oligonucleotide is labeled with a donor, the donor may interact with four complementary acceptors on the four chain terminators. Likewise, if the oligonucleotide is labeled with an acceptor, the acceptor may interact with four complementary donors on the four chain terminators.

The donor and acceptor groups may independently be selected from suitable fluorescent groups, chromophores and quenching groups. Donors and acceptors useful according to the invention include but are not limited to: 5-FAM (also called 5-carboxyfluorescein; also called Spiro (isobenzofuran-1(3H), 9'-(9H)xanthene)-5-carboxylic acid, 3',6'-dihydroxy-3-oxo-6-carboxyfluorescein); 5-Hexachloro-Fluorescein ([4,7,2',4',5',7'-hexachloro-(3',6'-dipivaloyl-fluoresceinyl)-6-carboxylic acid]); 6-Hexachloro-Fluorescein (-[4,7,2',4',5',7'-hexachloro-(3',6'-dipivaloylfluoresceinyl)-5-carboxylic acid-]); 5-Tetrachloro-Fluorescein (-[4,7,2',7'-tetra-chloro-(3',6'-dipivaloylfluoresceinyl)-5-carboxylic acid-]); 6-Tetrachloro-Fluorescein (-[4,7,2',7'-tetrachloro-(3',6'-dipivaloylfluoresceinyl)-6-carboxylic acid-]); 5-TAMRA (5-carboxytetramethylrhodamine; Xanthylium, 9-(2,4-dicarboxyphenyl)-3,6-bis(dimethyl-amino); 6-TAMRA (6-carboxytetramethylrhodamine; Xanthylium, 9-(2,5-dicarboxyphenyl)-3,6-bis(dimethylamino); EDANS (5-((2-aminoethyl) amino)naphthalene-1-sulfonic acid); 1,5-IAEDANS (5-((((2-iodoacetyl)amino)ethyl)amino) naphthalene-1-sulfonic acid); DABCYL (4-((4-(dimethylamino)phenyl)azo)benzoic acid) Cy5 (Indodicarbocyanine-5) Cy3 (Indo-dicarbocyanine-3); and BODIPY FL (2,6-dibromo-4,4-difluoro-5,7-dimethyl-4-bora-3a,4a-diaza-s-indacene-3-proprionic acid), Rox, as well as suitable derivatives thereof.

According to some methods of the invention, a chain terminator has been specifically labeled by a donor/acceptor that is different from the acceptor/donor that is present on the oligonucleotide probe. Preferred combinations of donors and acceptors are listed as, but not limited to, the donor/acceptor pairs shown in Tables 6 and 7 (which includes values for $R_o$ — the distance at which 50% of excited donors are deactivated by FRET).

TABLE 6

Typical values of $R_0$

| Donor | Acceptor | Ro (Å)* |
|---|---|---|
| Fluorescein | Tetramethylrhodamine | 55 |
| IAEDANS | Fluorescein | 46 |
| EDANS | DABCYL | 33 |
| Fluorescein | Fluorescein | 44 |
| BODIPY FL | BODIPY FL | 57 |

*$R_0$ is the distance at which 50% of excited donors are deactivated by FRET. Data from Haugland, RP. 1996. Handbook of Fluorescent Probes and Research Chemicals, 6th edition. Molecular Probes, Inc. Eugene OR, USA.

TABLE 7

FRET-pairs suitable for use in the method of this invention.

| Donor | Acceptor |
|---|---|
| (a) Fluorescent donors | |
| Fluorescein | Tetramethylrhodamine |
| Fluorescein | Cy-3 |
| Fluorescein | Rox |
| EDANS | DABCYL |
| Dansyl | Fluorescein |
| Cy3 | Cy-5 |
| Tryptophan | AEDANS |
| Fluorescein | Tetramethyl rhodamine |
| Tetramethyl rhodamine | DABCYL |
| Fluorescein | DABCYL |
| DABCYL | Cy-3 |
| Fluorescein | Hexachlorofluorescein |
| Tetrachlorofluorescein | Cy-5 |
| (b) Luminescent donors | |
| Europium | Cy-5 |
| Terbium | Tetramethyl rhodamine |
| Terbium | Cy-3 |

Reference herein to "fluorescence", "fluorescent dye" or "fluorescent groups" or "fluorophores" include luminescence, luminescent groups and suitable chromophores, respectively. In the present invention, the polynucleotide chain terminator and oligonucleotide probe may be labeled with luminescent labels and luminescence resonance energy transfer is indicative of complex formation. Suitable luminescent probes include, but are not limited to, the luminescent ions of europium and terbium introduced as lanthium chelates (Heyduk & Heyduk, 1997). The lanthanide ions are also good donors for energy transfer to fluorescent groups (Selvin, 1995). Luminescent groups containing lanthanide ions can be incorporated into polynucleotides utilizing an 'open cage' chelator phosphoramidite. Table 6 gives some preferred luminescent groups.

In certain embodiments of the invention, the polynucleotide chain terminator and oligonucleotide probe may also be labeled with two chromophores, and a change in the absorption spectra of the label pair is used as a detection signal, as an alternative to measuring a change in fluorescence.

There is a great deal of practical guidance available in the literature for selecting of appropriate reporter-quencher pairs for particular probes, as exemplified by the following references: Clegg (1993, Proc. Natl. Acad. Sci., 90:2994–2998); Wu et al. (1994, Anal. Biochem., 218:1–13); Pesce et al., editors, *Fluorescence Spectroscopy* (1971, Marcel Dekker, New York); White et al., *Fluorescence Analysis: A Practical Approach* (1970, Marcel Dekker, New York); and the like. The literature also includes references providing exhaustive lists of fluorescent and chromogenic molecules and their relevant optical properties for choosing reporter-quencher pairs, e.g., Berlman, *Handbook of Fluorescence Spectra of Aromatic Molecules*, 2nd Edition (1971, Academic Press, New York); Griffiths, *Colour and Constitution of Organic Molecules* (1976, Academic Press, New York); Bishop, editor, *Indicators* (1972, Pergamon Press, Oxford); Haugland, *Handbook of Fluorescent Probes and Research Chemicals* (1992 Molecular Probes, Eugene) Pringsheim, *Fluorescence and Phosphorescence* (1949, Interscience Publishers, New York), all of which incorporated hereby by reference. Further, there is extensive guidance in the literature for derivatizing reporter and quencher molecules for covalent attachment via common reactive groups that can be added to an oligonucleotide, as exemplified by the following references, see, for example, Haugland (cited above); Ulhman et al., U.S. Pat. No. 3,996, 345; Khanna et al., U.S. Pat. No. 4,351,760, all of which hereby incorporated by reference.

Exemplary reporter-quencher pairs may be selected from xanthene dyes, including fluoresceins, and rhodamine dyes. Many suitable forms of these compounds are widely available commercially with substituents on their phenyl moieties which can be used as the site for bonding or as the bonding functionality for attachment to an oligonucleotide. Another group of fluorescent compounds are the naphthylamines, having an amino group in the alpha or beta position. Included among such naphthylamino compounds are 1-dimethylaminonaphthyl-5-sulfonate, 1-anilino-8-naphthalene sulfonate and 2-p-touidinyl-6-naphthalene sulfonate. Other dyes include 3-phenyl-7-isocyanatocoumarin, acridines, such as 9-isothiocyanatoacridine and acridine orange; N-(p-(2-benzoxazolyl)phenyl)maleimide; benzoxadiazoles, stilbenes, pyrenes, and the like.

The reporter and quencher molecules may be selected from fluorescein and rhodamine dyes. These dyes and appropriate linking methodologies for attachment to oligonucleotides are described in many references, e.g., Marshall, Histochemical J., 7: 299–303 (1975); Menchen et al., U.S. Pat. No. 5,188,934; Menchen et al., European Patent Application 87310256.0; and Bergot et al., International Application PCT/US90/05565. All are hereby incorporated by reference.

There are many linking moieties and methodologies for attaching labeling molecules (e.g., a member of an interactive labels) to the 5' or 3' termini of oligonucleotides, as exemplified by the following references: Eckstein, editor, *Oligonucleotides and Analogues: A Practical Approach* (IRL Press, Oxford, 1991); Zuckerman et al., Polynucleotides Research, 15: 5305–5321 (1987) (3' thiol group on oligonucleotide); Sharma et al., Polynucleotides Research, 19: 3019 (1991) (3' sulfhydryl); Giusti et al., *PCR Methods and Applications*, 2: 223–227 (1993) and Fung et al., U.S. Pat. No. 4,757,141 (5' phosphoamino group via Aminolink.TM. II available from Applied Biosystems, Foster City, Cafil.) Stabinsky, U.S. Pat. No. 4,739,044 (3' aminoalkylphosphoryl group); Agrawal et al., Tetrahedron Letters, 31: 1543–1546 (1990) (attachment via phosphoramidate linkages); Sproat et al., Polynucleotides Research, 15: 4837 (1987) (5' mercapto group); Nelson et al., Polynucleotides Research, 17: 7187–7194 (1989) (3' amino group); and the like.

Preferably, an oligonucleotide probe is linked to a member of a pair of interactive labels at its 5' end. Also preferably, the 3' terminal of the oligonucleotide probe is blocked by a phosphate to prevent template independent elongation.

Measurable Changes

In the method of the present invention, the labeled oligonucleotide probe is capable of binding to a elongation chain comprising a labeled polynucleotide chain terminator or a labeled deoxynucleotide, thereby forming a complex in which the donor present on one molecule comes into proximity with the acceptor on the other molecule. This results in altered (e.g., reduced) fluorescence of the complex compared to the uncomplexed fluorescence exhibited by the oligonucleotide probe and/or polynucleotide chain terminator when free in solution.

In the method of the invention, fluorescence intensity of the oligonucleotide probe, the fluorescence intensity of the chain terminator and the fluorescence intensity of the complex is measured at one or more wavelengths with a fluorescence spectrophotometer, microtitre plate reader or real time PCR instruments. It is generally preferred that the oligonucleotide probe and the elongating chain comprising a chain terminator form a one-to-one complex and equal molar concentrations of oligonucleotide probe and chain terminator are present in the binding reaction. However, an excess of one reagent may be used without departing from the scope of the invention.

Typically, it is preferable to look for a signal (a positive), rather than for the absence of a signal (a negative) in an assay of the invention, but it will be appreciated that either or both may be followed. The preferred method for generating a detectable signal, according to the invention, is FRET. The advantage to FRET is that a new light wavelength is created. It is easier to detect a small signal above background than to detect a small decrease in a large signal. If future energy transfer reactions were to be developed, such as magnetic resonance energy transfer, or biological resonance energy transfer (as between green fluorescent protein and luciferase), such processes could also be used.

In some embodiments of the invention, fluorescence resonance energy transfer between the donor and acceptor may give rise to a distinct fluorescence emission spectrum of the complex which can be compared to the fluorescence emission spectra of the separate oligonucleotide probe and polynucleotide chain terminator molecules.

In some embodiments of the invention, signal generated by FRET is detected by steady state measurements of the integrated emission intensity of the donor (i.e., the fluorescent dye that is excited by the light source used in the spectral measurement) and/or the acceptor (i.e., the fluorescent dye which has a absorption spectrum that overlaps the emission spectrum of the donor). In addition, FRET may be detected by time—resolved measurements in which the decay of donor fluorescence is measured after a short pulse of excitation. In certain embodiments of the invention the donor is excited at a wavelength that does not itself result in efficient excitation of the acceptor, and FRET is detected by measuring the excitation of the acceptor due to transfer of a photon from the donor.

In some embodiments, the signal is generated by quenching and then detected by fluorescent readers. Any FRET (e.g., black hole) or non-FRET (e.g., Dabcyl) quenchers may be used as quencher-reporter pair for the present invention.

Fluorescent reporter molecule—quencher molecule pairs have been incorporated onto oligonucleotide probes in order to monitor biological events based on the fluorescent reporter molecule and quencher molecule being separated or brought within a minimum quenching distance of each other (see, for example, U.S. Pat. Nos. 6,030,78, and 5,795,729, each of which incorporated hereby in its entirety).

In some embodiments of the invention, the donor-acceptor pair is replaced by a receptor-quencher pair. It is not critical to the invention whether the oligonucleotide probe or a chain terminator is labeled with a quenching molecule so long as the other is labeled with a corresponding receptor molecule of a receptor-quencher pair. For example, probes can be developed where the intensity of the reporter molecule fluorescence increases due to the separation of the reporter molecule from the quencher molecule. Probes can also be developed which lose their fluorescence because the quencher molecule is brought into proximity with the reporter molecule. These reporter—quencher molecule pair probes can be used to detect the presence and identity of an incorporated chain terminator by monitoring either the appearance or disappearance of the fluorescence signal generated by the reporter molecule.

In one embodiment, the oligonucleotide probe comprises a quencher molecule, such that the quenching would quench signal from the primer—bound terminator. For example, the oligonucleotide probe is labeled with a dark quencher (e.g., a black hole quencher, BHQ) that absorbs or quenches fluorescence emitted by a receptor molecule (e.g., FAM). The BHQ dyes are a new class of dark quenchers that prevent fluorescence until a hybridization event occurs. In addition, these new dyes have no native fluorescence, virtually eliminating background problems seen with other quenchers. BHQ Dyes can be used to quench almost all reporter dyes and are commercially available, for example, from Biosearch Technologies, Inc (Novato, Calif.). The receptor fluorophore is used to label a chain terminator. Thus, incorporation of a chain terminator into the oligonucleotide primer and the hybridization of the oligonucleotide probe to the oligonucleotide primer bring the quencher molecule and the receptor molecule into close proximity. The quencher molecule quenches the fluorescent signal emitted from the receptor molecule and results in a decrease in fluorescent signal generated by FRET.

Preferably, reporter molecules are fluorescent organic dyes derivatized for attachment to the terminal 3' carbon or terminal 5' carbon of the probe or a chain terminator via a linking moiety. Preferably, quencher molecules are also organic dyes, which may or may not be fluorescent, depending on the embodiment of the invention. For example, in a preferred embodiment of the invention, the quencher molecule is a black hole quencher. Generally whether the quencher molecule is fluorescent or simply releases the transferred energy from the reporter by non-radiative decay, the absorption band of the quencher should substantially overlap the fluorescent emission band of the reporter molecule. Non-fluorescent quencher molecules that absorb energy from excited reporter molecules, but which do not release the energy radiatively, are referred to in the application as chromogenic molecules.

In one embodiment of the invention, the change of signal is measured using a spectrofluorophotometer.

Useful DNA Polymerases for the Invention

A wide variety of DNA polymerases maybe used in the subject methods. Suitable DNA polymerases for use in the subject methods may or may not be thermostable. DNA polymerases having mutations that reduce discrimination against the incorporation of chain terminators that are 2',3'-dideoxynucleotides (ddNTP) as compared with nucleotide triphosphates are preferred. Particularly preferred is the use of JDF-3 DNA polymerase mutants with reduced discrimination against ddNTP incorporation. Preferably, the JDF-3 DNA polymerase is also deficient in 3' to 5' exonuclease activity. A detailed description for suitable JDF-3 mutants can be found in U.S. patent application with Ser. No. 09/896,923, incorporated herein by reference.

In a preferred embodiment of the present invention, the JDF-3 DNA polymerase comprises one or more mutation at corresponding amino acids D141, E143, A485, L408 and P410.

In a more preferred embodiment, the JDF-3 DNA polymerase has one or more amino acid mutations selected from the group consisting of: D141A or D141T, E143A, L408H or L408F, A485T, and P410L.

In still another preferred embodiment, the JDF-3 DNA polymerase comprises four amino acid mutations of D141A, E 143A, P410L and A485T.

Taq DNA polymerase mutants having a Tyr residue at position 667 (numbered with reference to Taq DNA polymerase) may be used. A detailed description of such mutants can be found in U.S. Pat. No. 5,614,365, hereby incorporated by reference.

Methods for Generating DNA Polymerase Mutants with Reduced Discrimination

U.S. patent application Ser. Nos. 09/698,341, filed Oct. 27, 2000 and 09/896,923, filed Jun. 29, 2001 describe methods for making DNA polymerases with reduced discrimination toward non-conventional nucleotides (incorporated herein by reference). Random or site-directed mutants generated as known in the art or as described herein and expressed in bacteria may be screened for reduced discrimination against non-conventional nucleotides by several different assays. In one method, DNA polymerase proteins expressed in lytic lambda phage plaques generated by infection of host bacteria with expression vectors based on, for example, Lambda ZapII®, are transferred to a membrane support. The immobilized proteins are then assayed for polymerase activity on the membrane by immersing the membranes in a buffer containing a DNA template and the unconventional nucleotides to be monitored for incorporation.

Mutant polymerase libraries may be screened using a variation of the technique used by Sagner et al (Sagner, G., Ruger, R., and Kessler, C. (1991) *Gene* 97:119–123). For this approach, lambda phage clones are plated at a density of 10–20 plaques per square centimeter. Proteins present in the plaques are transferred to filters and moistened with polymerase screening buffer (50 mM Tris (pH 8.0), 7 mM $MgCl_2$, 3 mM $\mu$-ME). The filters are kept between layers of plastic wrap and glass while the host cell proteins are heat-inactivated by incubation at 65° C. for 30 minutes. The heat-treated filters are then transferred to fresh plastic wrap and approximately 35 $\mu$l of polymerase assay cocktail are added for every square centimeter of filter. The assay cocktail consists of 1× cloned Pfu (cPfu) magnesium free buffer (1× buffer is 20 mM Tris-HCl (pH 8.8), 10 mM KCl, 10 mM $(NH4)_2SO_4$, 100 ug/ml bovine serum albumin (BSA), and 0.1% Triton X-100; Pfu Magnesium-free buffer may be obtained from Stratagene (Catalog No. 200534)), 125 ng/ml activated calf thymus or salmon sperm DNA, 1.29 μCi/ml α-$^{33}$P ddNTP or dideoxynucleotides (at a dNTP:dye-ddNTP ratio of 1:15). Initial screening was done in the presence of MnCl$_2$, but the preferred method was to screen in 1× Taq Polymerase buffer (1.5 mM MgCl$_2$) The filters are placed between plastic wrap and a glass plate and then incubated at 65° C. for one hour, and then at 70° C. for one hour and fifteen minutes. Filters are then washed three times in 2×SSC for five minutes per wash before rinsing twice in 100% ethanol and vacuum drying. Filters are then exposed to X-ray film (approximately 16 hours), and plaques that incorporate label are identified by aligning the filters with the original plate bearing the phage clones. Plaques identified in this way are re-plated at more dilute concentrations and assayed under similar conditions to allow the isolation of purified plaques.

In assays such as the one described above, the signal generated by the label is a direct measure of the activity of the polymerase with regard to that particular unconventional nucleotide or combination of unconventional nucleotides used in the assay. Unconventional nucleotides corresponding to all four conventional nucleotides may be included in the reactions, or, alternatively, only one unconventional nucleotide may be included to assess the effect of the mutation(s) on utilization of a given unconventional nucleotide. One approach is to use unconventional nucleotides corresponding to all four nucleotides in a first screen to identify clones that incorporate more than a reference wild-type clone, and then to monitor the incorporation of individual unconventional nucleotides in a subsequent screen. In the preferred screening mode, only the dideoxynucleotides and dideoxynucleotide analogs of ddATP, ddCTP, and ddTTP would be used since ddGTP is not discriminated against by some DNA polymerases and increases the background signal of any screen In order to screen for clones with enhanced ability to incorporate dideoxynucleotides, clones identified in first screens utilizing only dideoxynucleotides may then be characterized by their sensitivity to low levels of each of the four dideoxynucleotides in a DNA polymerase nucleotide incorporation assay employing all four dNTPs, H-TTP tracer, and a low level of each ddNTP. Since incorporation of dideoxynucleotides stops DNA chain elongation, superior ability to incorporate dideoxynucleotides diminishes the incorporation of tritium labeled deoxynucleotides relative to wild-type DNA polymerase. Comparisons of ddNTP concentrations that bring about 50% inhibition of nucleotide incorporation ($I_{50\%}$) can be used to compare ddNTP incorporation efficiency of different polymerases or polymerase mutants. Comparisons of $I_{50\%}$ values for ddATP, ddCTP, ddGTP, and ddTTP can be used to identify mutants with reduced selectivity for particular bases. Such mutants would be expected to produce more uniform DNA sequencing ladders.

In order to measure incorporation of individual ddNTPs, cocktails are prepared which consist of varying concentrations of the ddNTP of interest, and a total of 200 μM of each nucleotide triphosphate. For example, the incorporation of ddATP by wild type JDF-3 polymerase may be measured at 0, 40, 80, 120 and 160 μM ddATP. In these reactions, dATP concentrations would be adjusted to 200, 160, 120, 80, and 40 μM, respectively, so that the total amount of adenine nucleotide triphosphate is 200 μM. In comparison, mutants may be assayed using ddATP concentrations of 0, 5, 10, and 20 μM ddATP, and adjusted dATP concentrations of 200, 195, 190, and 180 μM, respectively (dATP+ddATP=200 μM). Additional cocktails are prepared to similarly measure ddCTP, ddGTP, and ddTTP incorporation.

Incorporation of nucleotides under the concentration parameters described above may be measured in extension reactions by adding, for example, 1 μl of appropriately diluted bacterial extract (i.e., heat-treated and clarified extract of bacterial cells expressing a cloned polymerase or mutated cloned polymerase) to 10 μl of each nucleotide cocktail, followed by incubation at 72° C. for 30 minutes. Extension reactions are quenched on ice, and then 5 μl aliquots are spotted immediately onto DE81 ion-exchange filters (2.3 cm; Whatman #3658323). Unincorporated label is removed by 6 washes with 2×SCC (0.3M NaCl, 30 mM sodium citrate, pH 7.0), followed by a brief wash with 100% ethanol. Incorporated radioactivity is then measured by scintillation counting. Reactions that lack enzyme are also set up along with sample incubations to determine "total cpms" (omit filter wash steps) and "minimum cpms"(wash filters as above).

Cpms bound is proportional to the amount of polymerase activity present per volume of bacterial extract. The volume of bacterial extract (generally about 0.25–1 μl) which brings about incorporation of approximately 10,000 cpms is determined for use in subsequent nucleotide analog incorporation testing.

Genes for mutant DNA polymerases generated by random mutagenesis may be sequenced to identify the sites and number of mutations. For those mutants comprising more than one mutation, the effect of a given mutation may be evaluated by introduction of the identified mutation to the DNA polymerase gene by site-directed mutagenesis in isolation from the other mutations borne by the particular mutant. Screening assays of the single mutant thus produced will then allow the determination of the effect of that mutation alone.

Expression of Mutated DNA Polymerase According to the Invention

Methods known in the art may be applied to express and isolate the mutated forms of DNA polymerase according to the invention. Many bacterial expression vectors contain sequence elements or combinations of sequence elements allowing high level inducible expression of the protein encoded by a foreign sequence. For example, as mentioned above, bacteria expressing an integrated inducible form of the T7 RNA polymerase gene may be transformed with an expression vector bearing a mutated DNA polymerase gene linked to the T7 promoter. Induction of the T7 RNA polymerase by addition of an appropriate inducer, for example, isopropyl-β-D-thiogalactopyranoside (IPTG) for a lac-inducible promoter, induces the high level expression of the mutated gene from the T7 promoter (see Gardner & Jack, 1999, supra).

Appropriate host strains of bacteria may be selected from those available in the art by one of skill in the art. As a non-limiting example, E. coli strain BL-21 is commonly used for expression of exogenous proteins since it is protease deficient relative to other strains of E. coli. BL-21 strains bearing an inducible T7 RNA polymerase gene include WJ56 and ER2566 (Gardner & Jack, 1999, supra). For situations in which codon usage for the particular polymerase gene differs from that normally seen in E. coli genes, there are strains of BL-21 that are modified to carry tRNA genes encoding tRNAs with rarer anticodons (for example, argU, ileY, leuW, and proL tRNA genes), allowing high efficiency expression of cloned protein genes, for example, cloned archaeal enzyme genes (several BL21-CODON PLUS™ cell strains carrying rare-codon tRNAs are available from Stratagene, for example).

There are many methods known to those of skill in the art that are suitable for the purification of a modified DNA polymerase of the invention. For example, the method of Lawyer et al. (1993, PCR Meth. & App. 2: 275) is well suited for the isolation of thermostable DNA polymerases expressed in *E. coli*, as it was designed originally for the isolation of Taq polymerase. Alternatively, the method of Kong et al. (1993, J. Biol. Chem. 268: 1965, incorporated herein by reference) may be used, which employs a heat denaturation step to destroy host proteins, and two column purification steps (over DEAE-Sepharose and heparin-Sepharose columns) to isolate highly active and approximately 80% pure thermostable DNA polymerase.

Chain Elongation-Primer Extension

The polynucleotide extension reactions employed in the subject methods are catalyzed by a DNA polymerase, preferably one with reduced discrimination against the incorporation of ddNTP. The reaction may be carried out by methods well known in the art, for example, as described in *Current Protocols in Molecular Biology* (1997, Ausubel et al., John Weley & Sons, Inc.).

In some embodiments, the reaction mixture for the primer extension reaction may comprise a labeled chain terminator in addition to a polynucleotide template and an oligonucleotide primer. The labeled chain terminator serves as a chain terminator for the extension reaction and also provides a member of the pair of interactive labels to interact with the other member of the same pair of interactive labels on a correspondingly labeled oligonucleotide probe.

In other embodiments of the invention, the reaction mixture comprises a labeled deoxynucleotide, an unlabeled chain terminator, in addition to a polynucleotide template and an oligonucleotide primer. The labeled deoxynucleotide provides a member of the pair of interactive labels to interact with the other member of the same pair of interactive labels on a correspondingly labeled oligonucleotide probe. The unlabeled chain terminator simply serves to terminate the primer extension reaction.

The reaction mixture may further comprise an oligonucleotide probe which hybridizes to the oligonucleotide primer.

After or during the polynucleotide extension reaction, the oligonucleotide probe hybridizes to the elongating chain comprising the oligonucleotide primer and a chain terminator, the products are analyzed so as to identify the detectable signal generated by the interaction between the two members of the pair of interactive labels used to label the chain terminator and the probe (e.g., by FRET).

Hybridization

Polynucleotide hybridization involves providing a denatured probe (e.g., the oligonucleotide probe) and polynucleotide(s) (e.g., the oligonucleotide primer) under conditions where the probe and its complementary polynucleotide can form stable hybrid duplexes through complementary base pairing. The polynucleotides that do not form hybrid duplexes are then washed away leaving the hybridized polynucleotides to be detected, typically through detection of an attached detectable label. In a preferred embodiment, the oligonucleotide probe hybridizes to an elongating chain comprising the oligonucleotide primer and an incorporated chain terminator so that the donor and the acceptor on each of the molecules come to close proximity to generate a detectable signal which is indicative of the identity of the chain terminator. It is generally recognized that polynucleotides are denatured by increasing the temperature or decreasing the salt concentration of the buffer containing the polynucleotides.

The stringency required is nucleotide sequence dependent and also depends upon the various components present during hybridization and/or washing. In preferred embodiments, high stringent hybridization/washing conditions are used. In one embodiment, the oligonucleotide probe and the oligonucleotide primer are hybridized in an aqueous solution containing 0.1×SSC and 0.2% SDS, at room temperature for 2–60 minutes, followed by incubation in a solution containing 0.1×SSC at room temperature for 2–60 minutes.

Under high stringency conditions, majority of the hybridization occurs only between molecules which comprise complementary sequences (such as between an oligonucleotide primer comprising a first sequence and a second sequence and an oligonucleotide probe comprising a third sequence which hybridizes to the second sequence). However, it is not required two molecules to be completely complementary in order to hybridize under high stringency conditions. Under low stringency conditions (e.g., low temperature and/or high salt) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

In some preferred embodiments of the invention, the probe is simply added into the amplification reaction mixture and the hybridization between the oligonucleotide probe and the primer comprising an incorporated labeled chain terminator is performed during the amplification reaction (e.g., a PCR reaction). This provides a homogenous assay method which does not require the purification the primer-probe complex from unincorporated chain terminators before detection.

In other embodiments of the invention, the hybridization between the oligonucleotide probe and the primer comprising an incorporated labeled chain terminator is performed after the chain elongation reaction.

The oligonucleotide probe may be a universal probe which hybridizes to the second sequence of the oligonucleotide primer, or it may be made hybridizable to each primer which comprises a first sequence.

Specific Binding Pair

A specific binding pair may be used to construct the tag and the anti-tag molecules of the invention. In one embodiment, instead of having a 5' tag nucleotide sequence, the oligonucleotide primer of the present invention comprises a 5' tag comprising a member of a specific binding pair (e.g., biotin). A corresponding anti-tag molecule can be a molecule (e.g., a polynucleotide, a protein or other molecules) comprising the other member of the specific binding pair (streptavidin). In this case, the interaction between the tag and the anti-tag molecules is not through nucleotide pairing, but through the interaction between the members of the specific binding pair. A donor or acceptor labeled chain terminator may be incorporated into the oligonucleotide primer according to the subject method of the invention. The anti-tag molecule is labeled with the complementary acceptor or donor of the pair of interactive labels, and the interaction between biotin on the elongated primer and the streptavidin on the anti-tag molecule will allow the donor and acceptor of the same pair of interactive labels to come to close proximity, therefore generating a FRET signal.

Biotinylation of a target molecule (e.g., a polynucleotide) is a well known procedure which may be accomplished through a number of known procedures. For example, a chain terminator or a polynucleotide may be biotinylated using 5' kinase reactions.

Pre-Treatment Before Measuring

Undesired labels that might cause high background or other problems during the measuring or analysis (e.g., unincoporated labeled chain terminators or unhybridized oligonucleotide probes) may be removed by several ways. The operability of the subject methods is not dependent upon the precise method of removal. In some embodiments of the invention, the elongating chains comprising the oligonucleotide and the incorporated chain terminator are separated from the target polynucleotide prior to or concurrent with the incubation with the oligonucleotide probe. Such separation may be achieved in a variety of ways, including, but not limited to, electrophoresis, separation of extended primers by binding to a solid phase via a binding moiety on the extendable primer, separation of the extended primers by binding a solid phase in a binding moiety on the labeled terminator, chromatography, and the like. Suitable electrophoretic detection and separation systems include systems designed for the simultaneous electrophoretic separation and detection of fluorescently labeled polynucleotides, e.g., automated DNA sequencers such as the PE Applied Biosystems (Foster City, Calif., USA) 310, 377, or 3700.

Any of a broad range of solid supports known in the art could effectively be used in methods of the invention. For example, streptavidin—coated solid supports are available commercially such as for example, streptavidin—coated magnetic beads available from Promega (Madison, Wis.) and streptavidin coated microtitre plates (Covalink) available from NUNC (Raskilde, Denmark) or Labsystems (Marlboro, Mass.).

Separation methodologies dependent on nonspecific physical—chemical properties may be employed. Preferred methodologies include those methodologies in which specific affinity interactions are utilized such as solid support based affinity chromatography.

The unincorporated labeled terminators may be removed by a variety of different methods. One embodiment of such removal methods is the adsorption of the unincorporated terminators, such as by QIAquick™ PCR purification kit spin column (Qiagen, Venlo, Netherlands). In a preferred embodiment of the invention, the unincorporated labeled terminators are separated on the basis of differential electrophoretic migration by altering the electrophoretic mobility properties of the unincorporated terminators. The electrophoretic mobility of the unincorporated labeled terminators may be altered by treating the terminators with an alkaline phosphatase, shrimp alkaline phosphatase being particular preferred.

It will be readily appreciated to those skilled in the art that the subject methods and compositions may readily be "multiplexed" so as to simultaneously perform multiple analyses in a single reaction mixture. For example, one can detect SBE products from different primers/target polynucleotide pairs simultaneously. This may be accomplished by using a different 5' sequence tag of the primer and oligonucleotide probe for each primer/target polynucleotide pair.

The invention also includes compositions for performing the subject methods of identifying a nucleotide at a predetermined location on a polynucleotide molecule for analysis. The compositions of the invention include mixtures that are formed in the course of performing the methods of the invention or compositions that may be formed in the process of preparing to perform methods of the invention. Examples of the subject composition include mixtures comprising the combinations of an oligonucleotide primer comprising a first and a second sequences and an oligonucleotide probe which hybridizes to the oligonucleotide primer. The oligonucleotide probe may be labeled with a first member of a pair of interactive labels. The composition may further comprise one or more polynucleotide chain terminators, each of which is labeled with a second member of the pair of interactive labels. The composition may also comprise a polynucleotide synthesis enzyme (e.g., a DNA polymerase) and reagents required for primer extension and hybridization between the probe and the primer. The primer or the probe in the subject composition may be coupled to a member of a specific binding pair to allow its separation from other reagents in the composition or the reaction mixture comprising the subject composition.

A subject composition may comprise an oligonucleotide comprising a first sequence and a covalently linked tag molecule, and a labeled anti-tag molecule which specifically interacts with the tag molecule on the oligonucleotide primer. The tag molecule is preferred to locate at the 5' terminal of the oligonucleotide primer.

The invention also includes kits for identifying a nucleotide at a predetermined location on a target polynucleotide. Embodiments of the subject kits include a plurality of reagents that may be used to identify nucleotides in accordance with the methods of the invention. Kits of the invention, in addition to the reagents, preferably include written instructions for performing the subject methods. The subject kit may comprise a labeled oligonucleotide probe or a labeled anti-tag molecule, and one or more labeled terminators. Kits are preferably packaged in a unit container and may contain the reagents in pre-measured amounts designed to operate with each other so as to produce the desired result. The kits may further comprise one or more of the following items, DNA polymerase, alkaline phosphatase, chromatography columns, reaction buffers, amplification primers, exonuclease for degrading excess amplification primers, and hybridization/washing buffers.

EXAMPLES

Example 1

Detection of Nucleotide at Predetermined Position Using Probe Complementary to the Primer Detection of SNPs was also performed by FRET miniseqeunting using a probe which is filly complementary to the primer. The primer pBA was designed to anneal to pBluescflpt (A562C) so that the dideoxynucleotide to be incorporated is a ddCTP.

```
                                          (SEQ. ID. NO: 1)
pBA      5'-GGATGTGCTGCAAGGCGATT-3'

Figure 4:
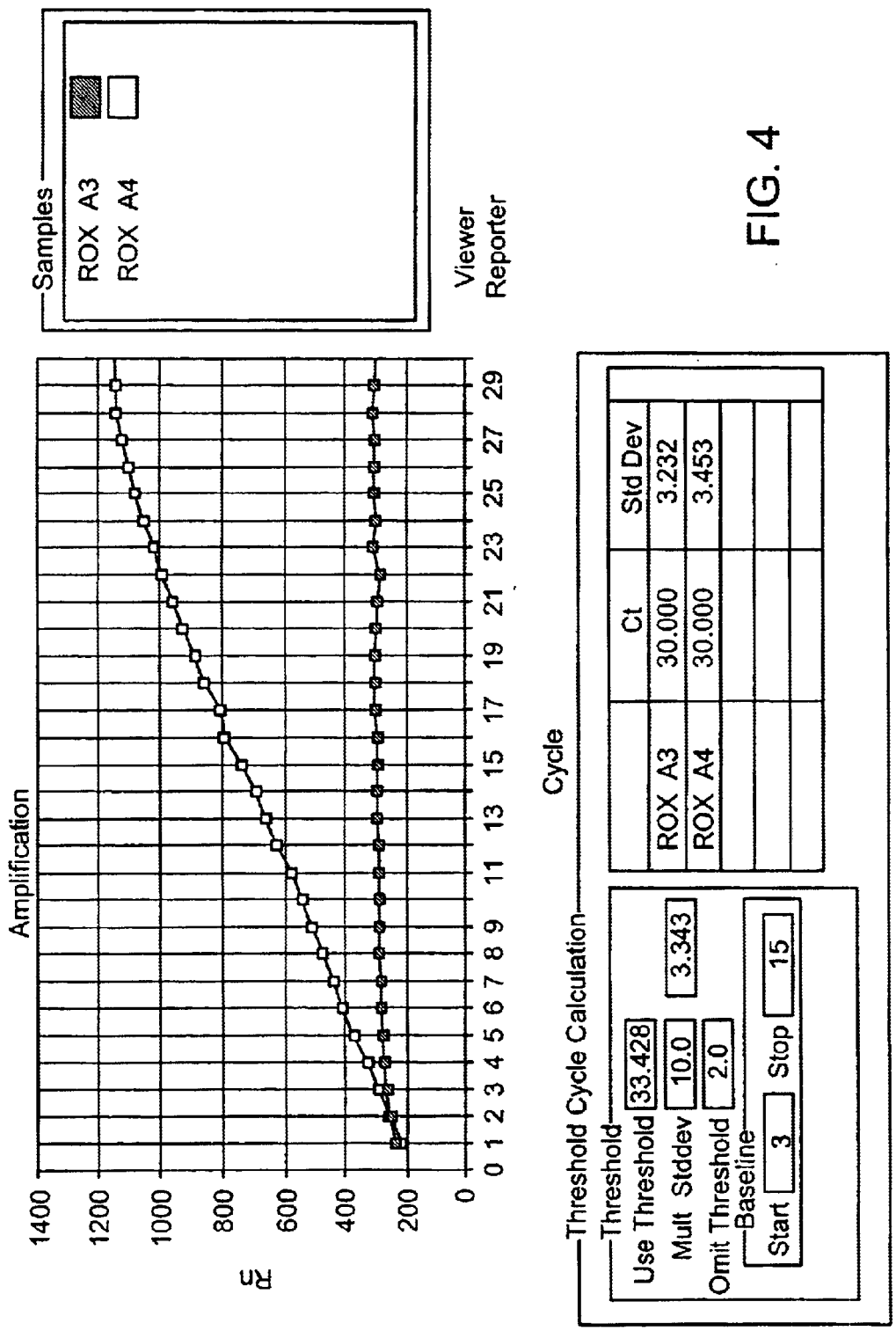
FIG. 4 illustrates that the positive control (A4 well) shows a ROX signal increase due to FRET from Fluorescein compared to the negative control (A3 well) according to one embodiment of the invention.

(SEQ. ID. NO: 2)
pAntiBA  3'-(P)CCTACACGACGTTCCGCTAA(F)-5'
``` pBA and pAntiBA were synthesized and HPLC purified by Genset Corporations (La Jolla, Calif.). pAntiBA20 was labeled with Fluorecein at 5'-end, and blocked with a phosphate group at its 3'-end. The relative orientation of the primers (above) are arranged to facilitate viewing of how they will hybridize to each other. 25 µl reactions contained 200 nM ROX-ddC, 4 U polymerase, 250 nM pBA 250 nM pAntiBA, and 200 nM pBluescript in 1× polymerase reaction buffer. Negative control lacked DNA template (pBluescript). Thermal cycling was performed in the Applied Biosystems Prism 7700 Sequence Detector. Thermal cycling conditions were performed by initial denaturing step at 95° C. for 2 minutes, followed by 30 cycles at 95° C. for 30 s, 50° C. for 1 min, and 57° C. for 30 s. The fluorescen were acquired during the annealing/extension phase of the primer extension cycles. The analysis was done using the multicomponent data from the Applied Biosystems 7700 Sequence Detector. FIG. 4 illustrates that the positive control (A4 well) shows a ROX signal increase due to FRET from Fluorescein compared to the negative control (A3 well).

Example 2
Detection of Nucleotide at Predetermined Position Using a Probe Partially Complementary to the Primer Detection of SNPs was also performed by FRET minisequencing using a probe which is partially complementary to the primer. The primer pJ was designed to anneal to pBluescript (A562C) so that the dideoxynucleotide to be incorporated is a ddCTP.

Oligos were synthesized and HPLC purified by Genset Corporations (La Jolla, Calif.). pAntiJ was labeled with Fluorecein at 5'-end, and blocked with a phosphate group at its 3'-end. The relative orientation of the primers (above) are arranged to facilitate viewing of how they will hybridize to each other.

Figure 5:
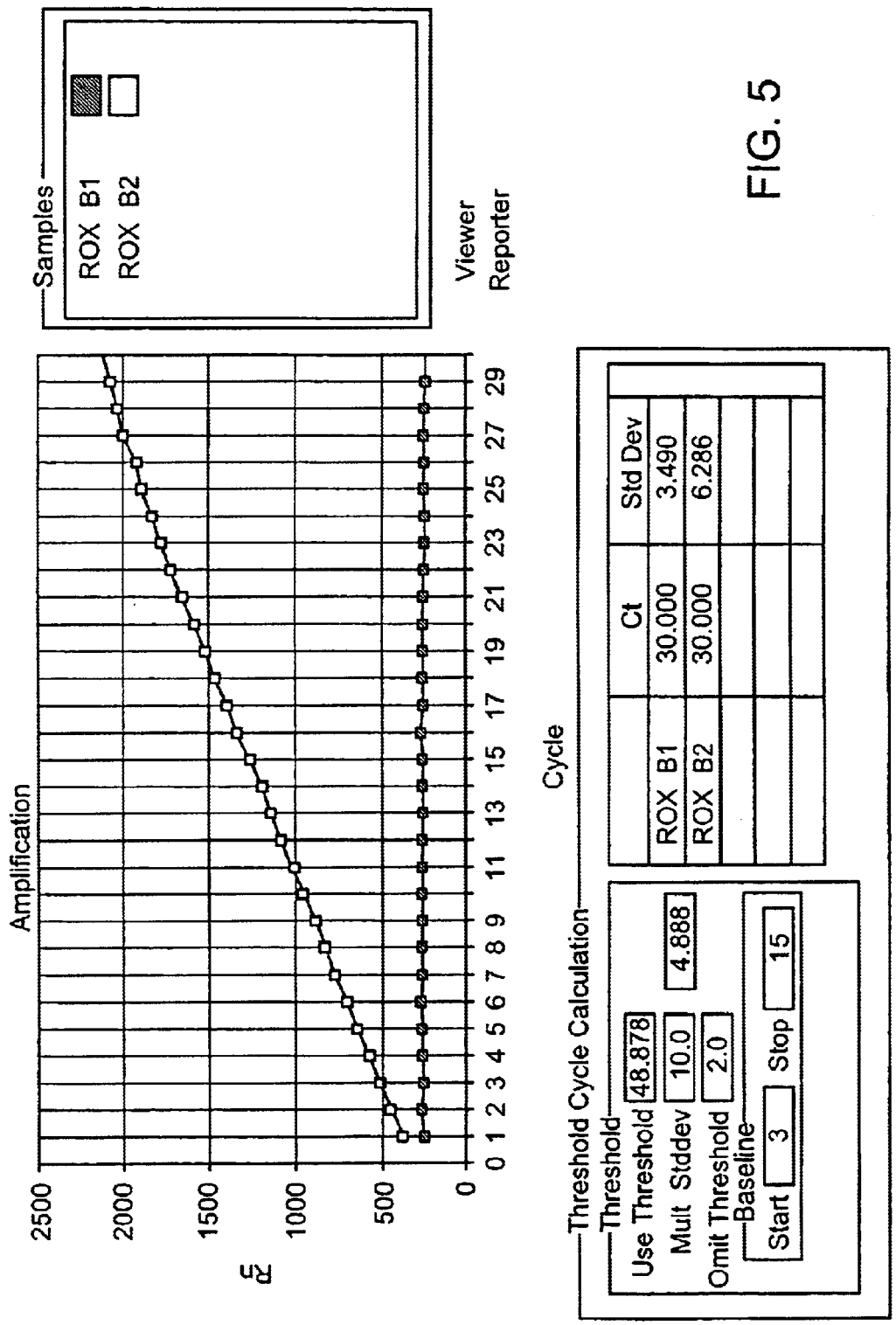
FIG. 5 illustrates that the positive control (B2 well) shows a ROX signal increase due to FRET from Fluorescein compared to the negative control (B1 well) according to one embodiment of the invention.

25 μl reactions contained 200 nM ROX-ddC, 4 U polymerase, 250 nM pJ 250 nM pAntiJ, and 200 nM pBluescript in 1× polymerase reaction buffer. Negative control lacked DNA template (pBluescript). Thermal cycling was performed in the Applied Biosystems Prism 7700 Sequence Detector. Thermal cycling conditions were performed by initial denaturing step at 95° C. for 2 minutes, followed by 30 cycles at 95° C. for 30 s, 50° C. for 1 min, and 57° C. for 30 s. The fluorescent intensities were acquired during the annealing/extension phase of the primer extension cycles. The analysis was done using the multicomponent data from the Applied Biosystems 7700 Sequence Detector. FIG. 5 illustrates that the positive control (B2 well) shows a ROX signal increase due to FRET from Fluorescein compared to the negative control (B1 well).

Figure 6:
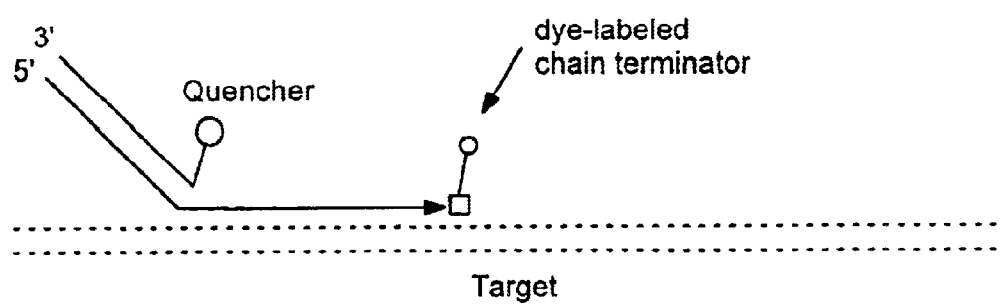
FIG. 6 illustrates the use of a quencher molecule according to one embodiment of the invention.

Example 3
Detection Of Nucleotide At Predetermined Position Usin2 a Quencher Molecule and a Probe Partially Complementary to the Primer Detection of SNPs was also performed by FRET munisequencing using a probe containing a quencher (FIG. 6). The primer pJ was designed to anneal to pBluescript (A562C) so that the dideoxynucleotide to be incorporated is a ddCTP.

pJ    5'-GAGGCTCGGAGCGGTTAAACGGATGTGCTGCAAGGCGATT-3'    (SEQ ID NO: 3)

Non-complementary to template    Complementary to template pAntiJ    3'-(P)CTCCGAGCCTCGCCAATTTG(F)-5'    (SEQ ID NO: 4)

TAOMAN was the first homogenous assay capable of detecting single nucleotide polymorphisms (U.S. Pat. No. 5,723,591). In this assay, two PCR primers flank a central probe oligonucleotide. The probe oligonucleotide comprises two fluorescent moieties. During the polymerization step of the PCR process, the polymerase cleaves the probe oligonucleotide. The cleavage causes the two fluorescent moieties to become physically separated, which causes a change in the wavelength of the fluorescent emission. As more PCR product is created, the intensity of the navel wavelength increases. While TaqMan accomplishes the goal of single nucleotide detection in a homogenous assay, it has two disadvantages. The first is that each nucleotide to be detected requires a different oligonucleotide probe comprising two different fluorescent moieties. Such probes must be custom-synthesized and are thus expensive. The second disadvantage is that TaqMan probes are not very discriminating for single nucleotide differences. Thus there can be significant false-positive signals.

Example 4
Detection of Nucleotide at Predetermined Position Using a Quencher Molecule and a Probe Partially Complementary to the Primer Detection of SNPs was also performed by FRET minisequencing using a probe containing a quencher (FIG. 6). The primer pJ was designed to anneal to pBluescript (A562C) so that the dideoxynucleotide to be incorporated is a ddCTP.

pJ    5'-GAGGCTCGGAGCGGTTAAACGGATGTGCTGCAAGGCGATT-3'    (SEQ ID NO: 3)

Non-complementary to template    Complementary to template pAntiJ-BHQ    3'-(P)CTCCGAGCCTCGCCAATTTG(BHQ2)-5'    (SEQ ID NO: 4)

pJ was synthesized and HPLC purified by Genset Corporations (La Jolla, Calif.). pAntiJ-BHQ was synthesized, labeled with Black Hole Quencher 2 (BHQ2) at its 5'-end, and blocked with a phosphate group at its 3'-end by Biosearch Technologies (Novato, Calif.). The relative orientation of the primers (above) are arranged to facilitate viewing of how they will hybridize to each other.

Figure 7:
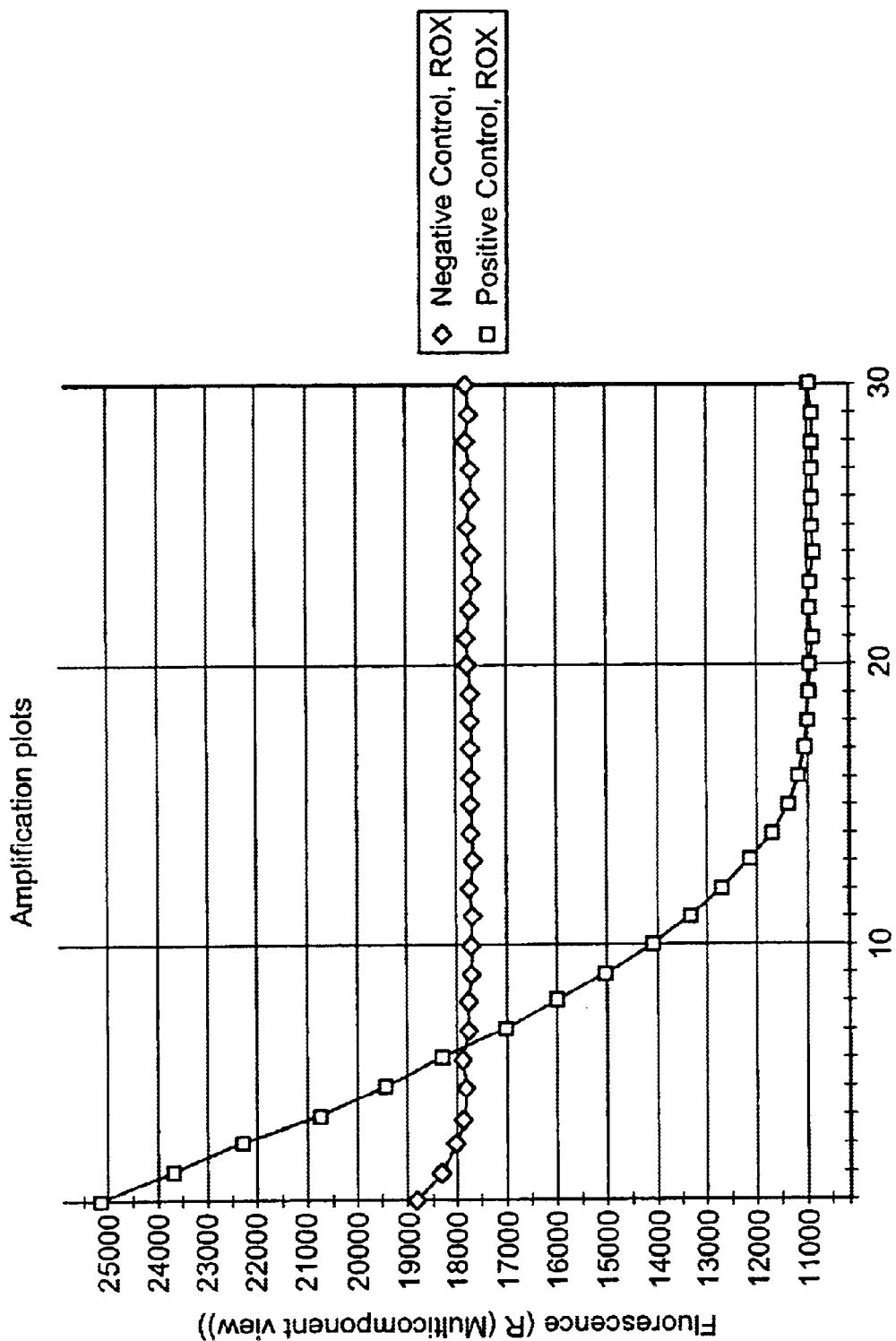
FIG. 7 demonstrates a ROX signal decrease for the positive control due to quenching of ROX fluorescence by BHQ2 upon incorporation of ROX-ddC according to one embodiment of the invention.

50 μl reactions contained 200 nM ROX-ddC, 4 U polymerase, 250 nM pJ, 250 nM pAntiJ-BHQ, and 200 nM pBluescript in 1× polymerase reaction buffer. Negative control lacked DNA template (pBluescript). Thermal cycling was performed in the Mx4000 QPCR system (Stratagene). Thermal cycling conditions were performed by initial denaturing step at 95° C. for 10 minutes, followed by 30 cycles at 95° C. for 30 s, 45° C. for 1 min, and 57° C. for 30 s. The fluorescent intensities were acquired during the annealing/extension phase of the primer extension cycles. The analysis was done using the multicomponent data from the Mx4000 QPCR system (Stratagene). FIG. 7 demonstrates a ROX signal decrease for the positive control due to quenching of ROX fluorescence by BHQ2 upon incorporation of ROX-ddC. Negative control lacks DNA template and therefore, no incorporation (no signal) is detected.

OTHER EMBODIMENTS

The foregoing examples demonstrate experiments performed and contemplated by the present inventors in making and carrying out the invention. It is believed that these examples include a disclosure of techniques which serve to both apprise the art of the practice of the invention and to demonstrate its usefulness. It will be appreciated by those of skill in the art that the techniques and embodiments disclosed herein are preferred embodiments only that in general numerous equivalent methods and techniques may be employed to achieve the same result.

All of the references identified hereinabove, are hereby expressly incorporated herein by reference to the extent that they describe, set forth, provide a basis for or enable compositions and/or methods which may be important to the practice of one or more embodiments of the present inventions.

What is claimed is:

1. A composition for identifying a nucleotide at a predetermined position of a target polynucleotide in a sample, said composition comprising:
   (a) an oligonucleotide primer comprising a first sequence which hybridizes to said target polynucleotide immediately 3' of said nucleotide, and a second sequence which does not hybridize to said target polynucleotide in the presence of a third sequence; and
   (b) an oligonucleotide probe comprising said third sequence which hybridizes to said second sequence of said oligonucleotide primer, said oligonucleotide probe labeled with a first member of a pair of interactive labels.

2. The composition of claim 1, further comprising a first polynucleotide chain terminator, which is incorporated in a template-dependent manner into said oligonucleotide primer by a polynucleotide synthesis enzyme.

3. The composition of claim 2, further comprising one or more of a second, a third and/or a fourth polynucleotide chain terminator, wherein said first, second, third and fourth polynucleotide terminators are not identical.

4. The composition of claim 2, wherein said first polynucleotide chain terminator is labeled with a second member of said pair of interactive labels.

5. The composition of claim 4, wherein said first and second members of said pair of interactive labels interact with each other to generate a signal by fluorescent resonance energy transfer.

6. The composition of claim 1, further comprising a template-dependent polynucleotide synthesis enzyme for incorporating in a template-dependent manner a complementary polynucleotide chain terminator into said oligonucleotide primer.

7. The composition of claim 6, wherein said polynucleotide synthesis enzyme is a JDF-3DNA polymerase.

8. The composition of claim 2, wherein said oligonucleotide primer comprises a separation moiety that permits separation of said oligonucleotide primer and/or said oligonucleotide probe hybridized to said primer from unincorporated polynucleotide chain terminator, and oligonucleotide probe which is not hybridized to said oligonucleotide primer.

9. The composition of claim 8, further comprising a target moiety specific for said separation moiety, wherein said separation moiety binds to said target moiety to permit said separation.

10. The composition of claim 9, wherein said target moiety is attached to a solid support.

11. The composition of claim 4, wherein said first and second members of said pair of interactive labels are fluorescent molecules which interact with each other to generate a signal by fluorescent resonance energy transfer.

12. A composition for identifying a nucleotide at a predetermined position of a target polynucleotide in a sample, said composition comprising:
   (a) an oligonucleotide primer comprising a first sequence which hybridizes to the target polynucleotide immediately 3' of said nucleotide, and is covalently attached to a tag molecule; and
   (b) an anti-tag molecule which binds to said tag molecule, said anti-tag molecule labeled with a first member of a pair of interactive labels.

13. The composition of claim 12, wherein said tag molecule is located on the 5' terminal of said oligonucleotide primer.

14. The composition of claim 13, wherein said tag molecule is a first member of a specific binding pair which comprises said first member and a second member.

15. The composition of claim 14, wherein said anti-tag molecule is said second member of said specific binding pair.

16. The composition of claim 15, wherein said specific binding pair is a biotin-streptavidin pair.

17. The composition of claim 1, wherein said second sequence is at the 5' terminal of said first sequence.

18. The composition of claim 1, further comprising a labeled conventional deoxynucleotide, and the other three unlabeled chain terminators, wherein said labeled conventional deoxynucleotide is incorporated into the oligonucleotide primer at a position corresponding to the predetermined nucleotide of the target polynucleotide.

19. The composition of claim 1, wherein one member of the pair of interactive labels is a quencher molecule.

20. A kit for identifying a nucleotide at a predetermined position of a target polynucleotide in a sample, said kit comprising:
   (a) an oligonucleotide primer comprising a first sequence which hybridizes to said target polynucleotide immediately 3' of said nucleotide, and a second sequence which does not hybridize to said target polynucleotide in the presence of a third sequence;
   (b) an oligonucleotide probe comprising said third sequence which hybridizes to said second sequence of said oligonucleotide primer, said oligonucleotide probe labeled with a first member of a pair of interactive labels; and
   (c) packaging materials therefore.

21. The kit of claim 20, further comprising a polynucleotide chain terminator, which can be incorporated in a template-dependent manner into said oligonucleotide primer by a polynucleotide synthesis enzyme.

22. The kit of claim 21, further comprising one or more of a second, a third and/or a fourth polynucleotide chain terminator, wherein said first, second, third and fourth polynucleotide terminators are not identical.

23. The kit of claim 21, wherein said polynucleotide chain terminator is labeled with a second member of said pair of interactive labels.

24. The kit of claim 20, further comprising a template-dependent polynucleotide synthesis enzyme for incorporating in a template-dependent manner a complementary polynucleotide chain terminator into said oligonucleotide primer.

25. The kit of claim 24, wherein said polynucleotide synthesis enzyme is a JDF-3 DNA polymerase.

26. A kit for identifying a nucleotide at a predetermined position of a target polynucleotide in a sample, said kit comprising:
   (a) an oligonucleotide primer comprising a first sequence which hybridizes to the target polynucleotide immediately 3' of said nucleotide, and is covalently attached to a tag molecule;
   (b) an anti-tag molecule which binds to said tag molecule, said anti-tag molecule being labeled with a first member of a pair of interactive labels; and
   (c) packaging materials therefore.

27. The kit of claim 26, wherein said tag molecule is a first member of a specific binding pair which comprises said first member and a second member.

28. The kit of claim 27, wherein said anti-tag molecule is said second member of said specific binding pair.

29. The kit of claim 28, wherein said specific binding pair comprises a biotin-streptavidin pair.

30. A method of identifying the presence of a nucleotide at a predetermined position of a target polynucleotide, said method comprising:

(a) incubating said target polynucleotide in a reaction mixture comprising an oligonucleotide primer comprising a first sequence which hybridizes to said target polynueleotide immediately 3' of said nucleotide and a second sequence which does not hybridize to said target polynucleotide in the presence of a third sequence, an oligonuolcotide probe comprising said third sequence which hybridizes to said second sequence of said oligonucleotide primer, said oligonucleotide probe labeled with a first member of a pair of interactive labels, a polynucleotide chain terminator labeled with a second member of said pair of interactive labels, wherein said incubating permits said polynucleotide chain terminator to be incorporated into said oligonucleotide primer, and permits said oligonucleotide probe to hybridize to said oligonucleotide primet to permit said pair of interactive labels to generate a signal; and (b) detecting said signal, wherein said detection is indicative of the presence of said nucleotide in said target polynucleotide.

31. A method of identifying the presence of a nucleotide at a predetermined position of a target polynuclceotide, said method comprising the steps:

(a) incubating said target polynucleotide in a reaction mixture comprising an oligonucleotide primer comprising a first sequence which hybridizes to said target polynucleotide immediately 3' of said nucleotide and a second sequence which does not hybridize to said target polynucleotide in the presence of a third sequence and a polynucleotide chain terminator labeled with a second member of a pair of interactive labels, wherein said incubating permits said polynucleotide chain terminator to be incorporated into said oligonucleotide primer;

(b) inctibating the oligonucleotide primer comprising said second member of said pair of interactive labels with an oligonucleotide probe comprising said third sequence which hybridizes to said second sequence of said oligonucleotide primer and said probe labeled with a first member of said pair of interactive labels, such chat formation of a hybrid between said oligonucleotide probe and said primer permits said pair of interactive labels to a generate a signal; and (c) detecting said signal, wherein said detection is indicative of the presence of said nucleotide in said target polynucleotide.

32. The method of claim 30 or 31, wherein said signal is generated by fluorescent resonance energy transfer.

33. The method of claim 30 or 31, wherein said oligonucleotide primer comprises a first sequence which hybridizes to said target polynucleotide and a second sequence which does not hybridize to said target polynucteotide in the presence of a third sequence.

34. The method of claim 33, wherein said oligonucleotide probe comprises said third sequence which hybridizes to said second sequence of said oligonucleotide primer.

35. The method of claim 30 or 31, wherein said polynucleotide chain terminator is incorporated by a polynucleotide synthesis enzyme.

36. The method of claim 30 or 31, wherein said reaction mixture further comprises one or mote of a second, a third and/or a fourth polynucleotide chain terminator, wherein said first, second, third and fourth polynucleotide terminators are not identical.

37. The method of claim 35, wherein said polynucleotide synthesis enzyme is a JDF-3 DNA polyrnerase.

38. The method of claim 33, wherein said second sequence is at the 5' terminal of said first sequence.

39. The method of claim 30 or 31, wherein said oligonucleotide primer comprises a separation moiety that permits separation of said oligonucleotide primer from said reaction mixture.

40. The method of claim 39, wherein a target moiety is provided for said separation moiety to form a specific binding pair for separation.

41. The method of claim 40, wherein said target moiety is attached to a solid support.

* * * * *

SEQUENCE LISTING

<160> NUMBER OF SEQ ID NOS: 4

<210> SEQ ID NO 1
<211> LENGTH: 20
<212> TYPE: DNA
<213> ORGANISM: Artificial sequence
<220> FEATURE:
<221> NAME/KEY: misc_feature
<222> LOCATION: (1)..(20)
<223> OTHER INFORMATION: Synthetic primer

<400> SEQUENCE: 1
ggatgtgctg caaggcgatt                                           20

<210> SEQ ID NO 2
<211> LENGTH: 20
<212> TYPE: DNA
<213> ORGANISM: Artificial sequence
<220> FEATURE:
<221> NAME/KEY: misc_feature
<222> LOCATION: (1)..(20)
<223> OTHER INFORMATION: Synthetic primer

<400> SEQUENCE: 2
cctacacgac gttccgctaa                                           20

<210> SEQ ID NO 3
<211> LENGTH: 40
<212> TYPE: DNA
<213> ORGANISM: Artificial sequence
<220> FEATURE:
<221> NAME/KEY: misc_feature
<222> LOCATION: (1)..(40)
<223> OTHER INFORMATION: Synthetic primer

<400> SEQUENCE: 3
gaggctcgga gcggttaaac ggatgtgctg caaggcgatt                     40

<210> SEQ ID NO 4
<211> LENGTH: 20
<212> TYPE: DNA
<213> ORGANISM: Artificial sequence
<220> FEATURE:
<221> NAME/KEY: misc_feature
<222> LOCATION: (1)..(20)
<223> OTHER INFORMATION: Synthetic primer

<400> SEQUENCE: 4
ctccgagcct cgccaatttg                                           20